US008807801B2

(12) United States Patent
Oldham et al.

(10) Patent No.: US 8,807,801 B2
(45) Date of Patent: Aug. 19, 2014

(54) TWO-PHOTON ENDOSCOPIC SCANNING ASSEMBLY FOR INFLAMMATORY DISEASE DETECTION

(75) Inventors: Kenn Oldham, Ann Arbor, MI (US); Thomas D. Wang, Ann Arbor, MI (US); Zhongyao Liu, Ann Arbor, MI (US); Jing Yong Ye, San Antonio, TX (US)

(73) Assignee: The Regents of the University of Michigan, Ann Arbor, MI (US)

( * ) Notice: Subject to any disclaimer, the term of this patent is extended or adjusted under 35 U.S.C. 154(b) by 155 days.

(21) Appl. No.: 13/356,286

(22) Filed: Jan. 23, 2012

(65) Prior Publication Data

US 2012/0270256 A1     Oct. 25, 2012

Related U.S. Application Data

(60) Provisional application No. 61/435,136, filed on Jan. 21, 2011.

(51) Int. Cl.
  *F21V 17/02*    (2006.01)
  *A61B 1/06*    (2006.01)

(52) U.S. Cl.
  USPC ............................ 362/319; 600/109; 600/160

(58) Field of Classification Search
  USPC ......... 600/182, 173, 160, 109, 129, 477, 478, 600/473, 476; 356/450; 362/319; 250/216, 250/227, 11, 227.26
  See application file for complete search history.

(56) References Cited

U.S. PATENT DOCUMENTS 4,291,958 A     9/1981 Frank et al.
6,485,413 B1 *  11/2002 Boppart et al. ............... 600/160

2003/0063838 A1   4/2003 Hagood et al.
2004/0254474 A1  12/2004 Seibel et al.
2008/0161648 A1   7/2008 Karasawa

OTHER PUBLICATIONS

International search report from PCT/US2012/022214 dated Aug. 24, 2012.
Bao et al. Fast handheld two-photon fluorescence microendoscope with a 475 micron x 475 micron field of view for in vivo imaging. Opt Lett 33:1333-1335 (2008).
Barnes et al., A characterization of the fluorescent properties of circulating human eosinophils. Photochem Photobiol, 58:297-303 (1993).
Bestvater et al. Two-photon fluorescence absorption and emission spectra of dyes relevant for cell imaging. J Microsc 208:108-115 (2002).
Bolzmacher et al., Displacement amplification of piezoelectric microactuators with a micromachined leverage unit. Sensors and Actuators, pp. 61-67 (2009).
Dela et al., Feasibility of using multiphoton excited tissue autofluorescence for in vivo human histopathology. Biomed Opt Express 1:1320-1330 (2010).
Denk et al., Two-photon laser scanning fluorescence microscopy. Science 248:73-76 (1990).

(Continued)

*Primary Examiner* — Thomas Sember
(74) *Attorney, Agent, or Firm* — Marshall, Gerstein & Borun LLP

(57) ABSTRACT

An endoscopic imaging device is described that achieves longitudinal axis (z-axis) scanning into a tissue or sample, using a piezoelectric microactuator. In some configurations, additional lateral (xy-plane) scanning is also achieved, to allow for the creation of full three-dimensional imaging, ex vivo or in vivo. The techniques may be used to image and diagnosis allergic rhinitis and eosinophilic esophagitis in tissue.

15 Claims, 21 Drawing Sheets

(56) References Cited

OTHER PUBLICATIONS

Engelbrecht et al. Ultra-compact fiber-optic two-photon microscope for functional fluorescence imaging in vivo. Optics Express 16:5556-5564 (2008).

Fu et al., Fibre-optic nonlinear optical microscopy and endoscopy. J Microsc, 226(Pt 3):195-206 (2007).

Helmchen et al., Deep tissue two-photon microscopy. Nat Methods, 2(12):932-940 (2005).

Hetrick et al., High amplification compliant microtransmission for rectilinear electrothermal actuators. Sensors Actuators A, 97-98:776-783 (2002).

Hong-Wen et al., Analysis of the displacement amplification ratio of bridge type flexure hinge. Sensors and Actuators, 132:730-736 (2006).

Hoy et al., Miniaturized probe for femtosecond laser microsurgery and two-photon imaging. Opt Express, 16(13):9996-10005 (2008).

Hubbard et al., Design and characterization of a dual-stage, thermally actuated nanopositioner.

Jung, et al., Miniaturized probe based on a microelectromechanical system mirror for multiphoton microscopy. Opt Lett, 33(12):1324-1326 (Jun. 2008).

Neumann et al. First description of eosinophilic esophagitis using confocal laser endomicroscopy (with video). Endoscopy 43(Suppl 2):E66 (2011).

Ono et al., Microassembly of pzt actuators into silicon microstructures. IEEJ Trans Sensors Micromachines, 129(12):471-472 (2009).

Peery et al. Variable reliability of endoscopic findings with white-light and narrow-band imaging for patients with suspected eosinophilic esophagitis. Clin Gastroenterol Hepatol 9:475-480 (2011).

Piyawattanametha, et al., In vivo brain imaging using a portable 2.9 g two-photon microscope based on a microelectromechanical systems scanning mirror. Opt Lett, 34(15):2309-2311 (2009).

Safdarian et al. Identification of nasal eosinophils using two-photon excited fluorescence. Ann Allergy Asthma Immunol 106:394-400 (2011).

Skala et al. In vivo multiphoton microscopy of NADH and FAD redox states, fluorescence lifetimes, and cellular morphology in precancerous epithelia. Proc Natl Acad Sci U S A 104:19494-19499 (2007).

Skala et al. Multiphoton microscopy of endogenous fluorescence differentiates normal, precancerous, and cancerous squamous epithelial tissues. Cancer Res 65:1180-1186 (2005).

Theer, et al., "Two-photon imaging to a depth of 1000 microm in living brains by use of a ti:al2o3 regenerative ampli?er," Opt Lett, 28(12):1022-1024 (2003).

Traina et al., A strain amplifying piezoelectric mems actuator. J Micromech Microeng, 17:781-787 (2007).

Yu et al., Mems flextensional actuator using lead zirconate titanate thin film. IEEE, pp. 375-378 (2005).

Zhao et al., Development of a versatile two-photon endoscope for biological imaging. Biomed Opt Express 1:1159-1172 (2010).

International Preliminary Report on Patentability from PCT/US2012/022214 dated Aug. 1, 2013.

\* cited by examiner

TWO-PHOTON ENDOSCOPIC SCANNING ASSEMBLY FOR INFLAMMATORY DISEASE DETECTION

STATEMENT REGARDING FEDERALLY SPONSORED RESEARCH OR DEVELOPMENT

This invention was made with government support under CA136429 awarded by the National Institutes of Health. The government has certain rights in the invention.

CROSS-REFERENCE TO RELATED APPLICATIONS

The present application claims the benefit of U.S. Provisional Application No. 61/435,136, entitled "Two-Photon Endoscopic Scanning Assembly for Inflammatory Disease Detection," filed on Jan. 21, 2011, which is hereby incorporated by reference herein in its entirety.

FIELD OF THE DISCLOSURE

The present disclosure relates generally to techniques for imaging tissue using an optical instrument and, more particularly, to techniques for allowing two-dimensional (2D) and three-dimensional (3D) scanning using an optical instrument.

BACKGROUND

The ability to perform endoscopic tissue imaging using a fiber-coupled two-photon laser has recently been demonstrated by several research groups. For many applications the size of the scanning mechanism for image creation is a limiting factor in system miniaturization. Many projects concentrate on automated x- and y-scanning, but a fast enough scanning mechanism parallel to the optical path could ultimately lead to 3-dimensional imaging of tissue structures in vivo, with novel diagnostic capabilities for allergic diseases and cancer.

SUMMARY OF THE INVENTION

The present techniques provide for a low-profile, piezoelectrically-driven microactuator able to achieve very large stroke lengths (along the z-axis/longitudinal axis) within size constraints suitable for certain endoscopic microscopy applications.

In some examples, the actuator relies upon the large work density of piezoelectric material to thereby covert a small-displacement, large-force motion into large displacement motion via a micromachined silicon assembly. The actuator may include a lever-arm and bridge-type amplification mechanism to achieve displacements large enough for substantial z-axis scanning. In some examples, the actuator utilizes an actuator having lever arm and chevron-beam structures to amplify high-force, low-displacement motion of a ceramic lead-zirconate-titanate (PZT) structure into large displacement of a translational platform that performs the scanning.

The actuators described herein may be used in any number of instruments and applications. For example, actuators may be paired with optical components to form an integrated device. These optical components may be integrated with one or more of the actuators using micromachined silicon flexures, to form a machined z-axis actuator. For example, actuators are described forming endoscopic instruments acting as two-photon microscopes, with an optical path occupying the center of the imaging system. Because the actuators are low-profile, they can be used in structures of typical endoscopic size, while still providing scanning depth ranges useful for microscopy. Actuators may be fit along the side of the optical path to minimize total cross-sectional area and volume of the scanning head used to generate images.

As a result, the present techniques may be used to form an optical instrument having an actuator mechanism that offers high image resolution and can image deep into tissue and to create volumetric images, where the instrument can be sized small enough to allow for arbitrary movement and manipulation into tissue contact. By providing a platform for scanning image collection in a miniature device (e.g., in hand-held or endoscopic form) diagnosis, monitoring, and studies that would be impossible with a benchtop system may not be achieved. With the present techniques, biological studies and medical monitoring in living organisms become possible. With the present techniques, an optical instrument can be maneuvered into the same location on tissue, over long periods of time, to monitor or study disease progression over time, in either humans or animal models. Whereas, benchtop systems, by contrast, are limited to single time samples from biopsies, or specific locations on an animal that happen to "fit" into the system. Further, other miniature microscopes, such as confocal microscopes, tend not to have as high resolution and are more prone to photo-bleaching and possibly disrupting the tissue, compared to short pulse, two-photon instruments as discussed herein.

More generally, the techniques have been applied to develop a multi-photon scanning assembly (e.g., microscope or endoscope) capable of imaging esophageal mucosa to identify and quantify eosinophilic esophagitis, allowing for an "optical biopsy" of a specimen in a nondestructive, label-free manner. In an example implementation, a multi-photon optical apparatus was formed having sensitivities to eosinophil autofluorescence from the mucosal surface, which was capable of distinguishing eosinophils from the surrounding squamous epithelium over a scanning depth. The techniques can be applied ex vivo or in vivo.

In accordance with an embodiment, an endoscopic device for illuminating a sample over a 3-dimensional volume, includes: a connector stage for receiving an input beam of short pulses; an xy-scanning stage coupled to receive the input beam of short pulses and scan the short pulses for movement in a lateral direction across an xy-plane of the sample; an actuator stage coupled to scan the short pulses for movement in a z-axis direction of the sample, where the actuator stage comprises a piezoelectric stage capable of producing a first displacement, an amplification stage mechanically coupled to the piezoelectric stage for amplifying the first displacement into a second displacement, and a lens mounting stage coupled to the amplification stage, where the piezoelectric stage, the amplification stage, and the lens mounting stage form an integrated MEMS assembly; and a lens mounted on the lens mounting stage for scanning the input beam across the 3-dimensional volume within the sample In some embodiments, the amplification stage includes a lever amplifier for translating piezoelectric movement into at least partially transverse movement and mechanically coupled to a chevron stage for translating and amplifying the translated movement into longitudinal movement.

In some examples, the piezoelectric stage is formed of a PZT assembly rigidly coupled to one end of a base and movably coupled to the amplification stage, wherein the amplification stage is positioned for movement along the base.

An external controller may be coupled to the xy-scanning stage and to the actuator stage to control scanning of the short pulses within the 3-dimensional volume of the sample, where that sample may be a biological sample, such as tissue, or a non-biological sample, such as a plastic, semiconductor, other material.

In accordance with another embodiment, a method of detecting a biomarker within a 3-dimensional volume of a sample, includes: providing an endoscopic assembly for producing a output laser energy, the endoscopic assembly comprising an xy scanning stage and an actuator stage for z-axis scanning within the sample; the xy scanning stage scanning the output laser beam over a planar scan area of the sample; the actuator stage scanning the output laser beam over a depth range of the sample, where the depth range and the planar scan area form the 3-dimensional volume, driving the actuator stage using a piezoelectric stage and mechanically amplifying a resulting displacement of the piezoelectric stage to scan the two-photon output beam over the entire depth range; sampling a plurality of points within the sample by collecting fluorescence resulting from interaction of the output laser beam and the sample at each of the points; and detecting the biomarker from the fluorescence collected from each the plurality of points.

DETAILED DESCRIPTION

Provided are techniques for forming an optical instrument having an actuator mechanism that offers high image resolution and can image deep into tissue to create volumetric images. The optical the instrument can be sized small enough to allow for arbitrary movement and manipulation into tissue contact. With the use of various actuator configurations and materials, low-profile scanning devices able to achieve large, high-speed displacement of optical components (e.g., mirrors or lenses) via microactuation allowing for real-time cross-sectional or 3D images of tissue. For example, as discussed, several types of novel imaging modalities may be used to achieve deep optical penetration (up to 500 µm or greater) into biological tissue, including dual-axes confocal microscopy and two-photon microscopy. Particular examples of a multi-photon scanning assembly described herein include a two-photon microscope optical instrument having actuators in accordance with techniques described herein and used for eosinophilic esophagitis and nasal rhinitis imaging and identification applications.

Figure 1:
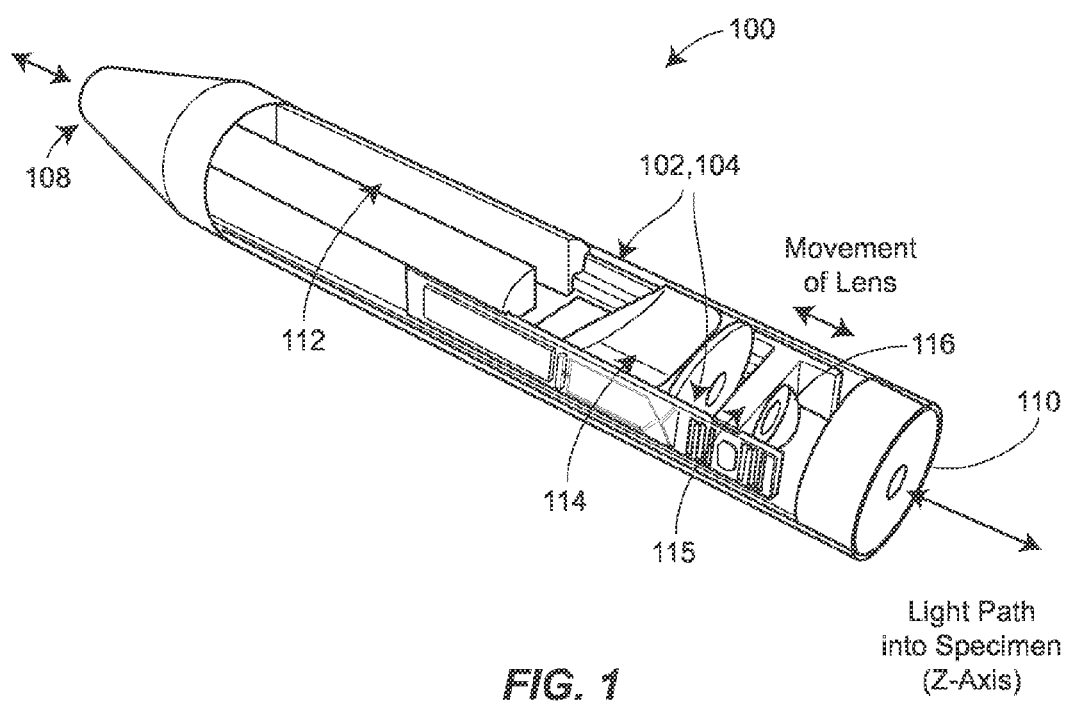
FIG. 1 illustrates an example 3D scanning optical instrument having low-profile piezoelectric actuators to provide z-axis scanning, in accordance with an example.

FIG. 1 illustrates an example 3-D scanning two-photon endoscope 100 having low-profile piezoelectric actuators 102 and 104. At a first end of a housing 106 (partially shown) a fiber connector 108 is provided for coupling to a single or multi-mode optical fiber. At a second end of the housing 106, a gradient index (GRIN) lens 110 (or other lens structure, whether a substantially flat compliant lens or otherwise) provides a light path for examining a specimen. The specimen can be tissue collected ex vivo; or the device may be used for in vivo testing. Extending from the first end is a channel 112 providing a compliance region for electrical connection to the actuators 102 and 104.

In the illustrated example the actuators 102 and 104 are microactuators, i.e., having features on the micron scale size, and are disposed on opposing sides of the endoscope 100, extend along a longitudinal axis (or z-axis) thereof. The actuators 102 and 104 convert electrical drive signals into large z-axis translational movement. An x-y scanning mirror stage 114 is disposed between the two microactuators 102 and 104, and operates to scan a lens holder 115. The x-y scanning mirror stage 114 may be used to scan the light path across a plane on top of up or below the specimen. To affect z-axis scanning, i.e., scanning into the tissue, the microactuators 102 and 104 are both movable to move the lens holder. In this way, the illustrated endoscope 100 provides full three dimensional control over position and scanning of a pulsed or continuous wave output light energy from the lens 110.

The endoscope 100 may be sized for various diagnostic applications. For example, for the illustrated example, the microactuators 102 and 104 were designed to have a cross-sectional area of approximately 3 mm by 0.6 mm or smaller, with a length less than 20 mm, to avoid increasing scanning head size of the endoscope 100. The microactuators 102 and 104 offer a longitudinal scanning range (i.e., along the z-axis) from 0 to 500 µm, and at an unloaded frequency of at least 100 Hz. This corresponded to real-time scanning of 10 Hz or better when the endoscope 100 was implemented with a 3 mm diameter, 0.12 g focusing lens 116. Depending on the size of the GRIN lens 110, the resultant scanning distance into adjacent tissue for a 500 µm capable displacement microactuator was between 0 and 220 µm. The amount of displacement depends on the input electrical signal. By way of example, for a 120 V input, a full range of 486 µm of motion has been achieved, along the z-axis, with a scanning frequency greater than 500 Hz.

To provide further aid and flexibility in structural support and compliance, translational platforms for the microactuators 102 and 104 may be supported by features that provide larger transverse and vertical stiffness even when the width of the microactuator is limited, features discussed herein such as common folded silicon flexures.

In operation, an incoming pulsed laser energy or CW laser energy is delivered by an optical fiber into the connector end 108. The laser energy is positioned into x- and y-direction by the scanning stage 114. The linear microactuators 102 and 104 are coupled to drive the scanning stage 114, which in turn moves a focal point of lens 116 along the z-axis inside tissue. In a multi-photon microscopy application, fluorescent light is generated at the focal point, e.g., through a two-photon absorption process, and collected by the endoscope 100, using the same optical setup, and sent to a photomultiplier tube through the optical fiber.

Using a mechanical configuration for the microactuators allows one to provide stroke lengths (z-axis displacement) and scanning speeds greater than that of conventional techniques. For example, for known large-displacement thermal actuator designs, scanning speed is limited by the thermal time constant; plus, the heat generated may be difficult to dissipate in vivo. Further, the piezoelectric stack actuators and DC-linear motors used in some miniaturized optical imaging systems do not meet the space requirements of an effective endoscope device. Further still, conventional electrostatic-based mechanisms suffer from limited force side-instability, and are thus limited against large displacements.

The microactuators may rely on the large work density of piezoelectric materials to convert a small-displacement of a piezoelectric material into large displacement motion, e.g., through a MEMS transmission structure. Piezoelectric materials have been chosen for forming at least a portion of the microactuator, because materials like PZT are capable of delivering high forces and can be operated at high speeds. As PZT movements are in the range of only a few micrometers (displacement below 1 per thousand of the PZTs length); and several hundreds of micrometers may be needed to adjust z-axis focusing of a lens. A large mechanical amplifier with PZT structures has thus been used in some examples described herein. The microactuator may be an optimized combination of lever-arm and bridge-type amplification mechanisms, producing combined effects having amplification ratios exceeding those previously described for fabricated MEMS devices. In addition, a folded flexure design allows for forming low profile actuators that are available for applications such as two-photon microscopy.

A comparison of the maximum stroke length, along the z-axis, cross-sectional scan area, scan frequency, and amplification factor, for an example of the present techniques, against other proposed endoscopic devices is provided in Table 1. As shown, the example configuration in FIG. 1 was able to achieve, for a 120 V input, a full range of 486 µm of maximum stroke, with a scanning frequency greater than 500 Hz and an amplification of 170×.

TABLE 1

| Source | Type | Max. Stroke (µm) | Cycle Freq. (Hz) | Cross-Sect. mm × mm | Amplification |
|---|---|---|---|---|---|
| Faulhaber [6] | DC Linear | 15000 | 300 | 6.8 × 6.8 | N/A |
| Henderson [7] | Piezo wiggle | 6000 | 5000 | 1.6 × 1.6 | N/A |
| Smith et al. [8] | Modified comb | 500 | unreported | 3 × 0.1 | N/A |
| Hubbard et al. [9] | Thermal | 52 | 230 | 2.5 × 1 | 3.5x |
| Conway et al. [10] | PZT | 1.4 | 5000 | 0.5 × 0.54 | 10x |
| Kota et al. [11] | Comb drive | 20 | 3880 | <0.01 × 2 | 12x |
| Sabr et al. [12] | PZT stack | 82 | 542 | 20 × 0.4 | 18x |
| Chu et al. [13] | Thermal | 100 | unreported | 2 × 2 | 21x |
| Su and Yang [14] | Comb drive | 10 | unreported | 0.7 × 0.7 | 148x |
| Current Paper | PZT Ceramic | 486 | 507 | 3 × 0.6 | 170x |

In some examples, the microactuator was designed as a multi-stage (e.g., three-stage) MEMS assembly having: a piezoelectric material to generate a motion; an amplification structure that transforms (e.g., amplifies) the motion; and a platform that allows the fixation and stabilization of a microlens. The second stage may be formed of a platform that uses lever-arm and chevron bridge-structures to transform/amplify the motion.

Figure 2:
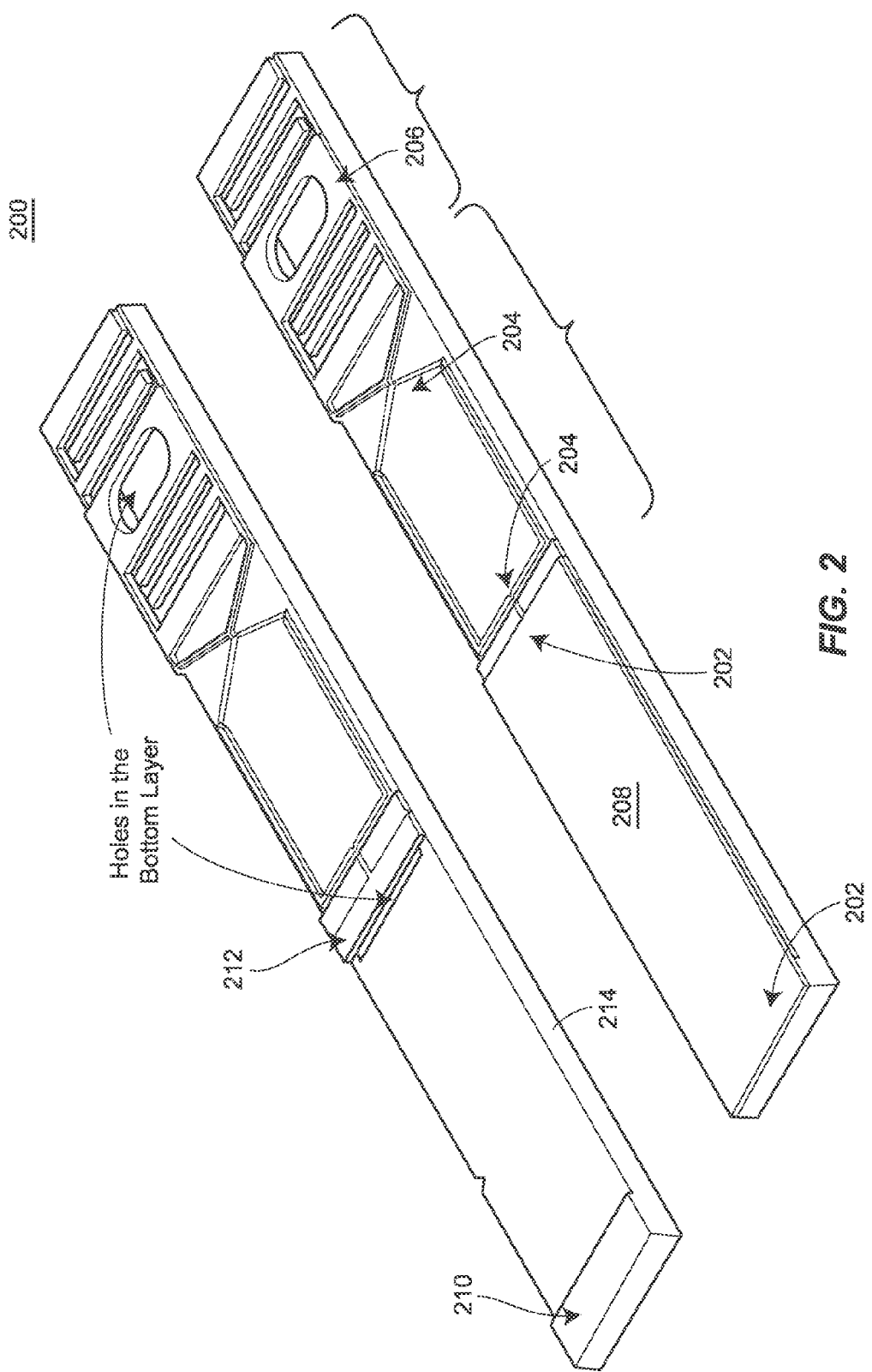
FIG. 2 illustrates an integrated multi-stage microactuator as may be used in FIG. 1 and having piezoelectric stage, an amplification stage, and a moveable platform stage.

FIG. 2 shows an integrated multi-stage microactuator 200 having a PZT stage 202, an amplification stage 204 and a lens platform 206, where the microactuator 200 is shown before a piezoelectric material 208 has been mounted and afterwards. The PZT stage 202 is formed by the PZT plate 208 attached to a gold plating of the microactuator at two anchor points 210 and 212. In the illustrated example, a glue attachment (e.g., a silver conductive adhesive may be used for the fixation of the piezoelectric stage) is used; although any suitable attachment mechanism, fixture structure, or fabrication technique may be used instead. In an example implementation, the dimensions of the PZT stage 202 were 150 µm×3 mm×10 mm; and the piezoelectric coefficient d31 was 2.1·10−10 C/N. Thus, when actuated at 110 V, a displacement of 1.5 µm was obtained against the stiffness of the transmission. To provide mechanical transfer, the attachment at base 210 may be rigid, such has a handle layer, while the attachment end 212 may be a movable platform in a base 214 capable of pushing or pulling on the mechanical amplifier stage 204.

Figure 3A:
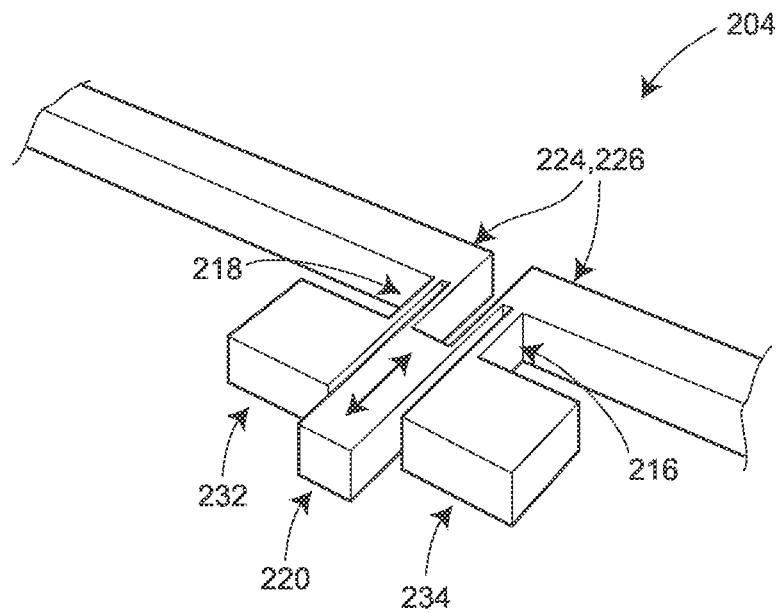
FIGS. 3A-3C provide different perspective views for an example amplification stage as may be used in microactuator of FIG. 2.
Figure 3B:
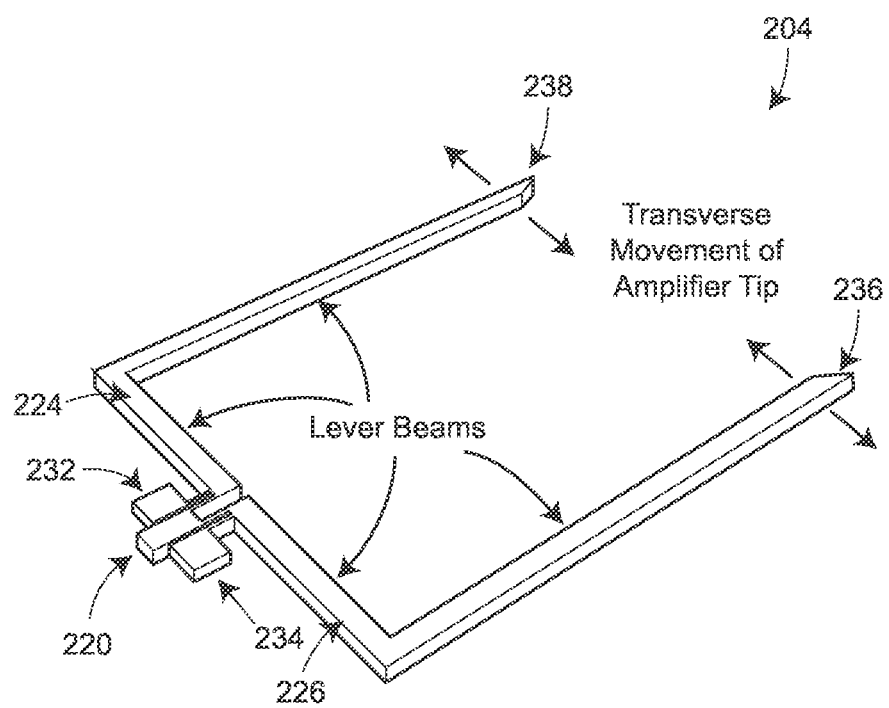

FIGS. 3a and 3b illustrate a first portion of the amplification stage 204. Two short, parallel springs 216 and 218 are placed a small distance apart, each having a first flexure 216A/218A connecting a piezoelectric activation nose 220 to lever-beams 224 and 226 and having a second flexure 228A/230A connecting lever-beams 224 and 225 to fixed bases 232 and 234. The nose 220 that is actuated by the piezoelectric plate 208, through the mounting 212.

Figure 3C:
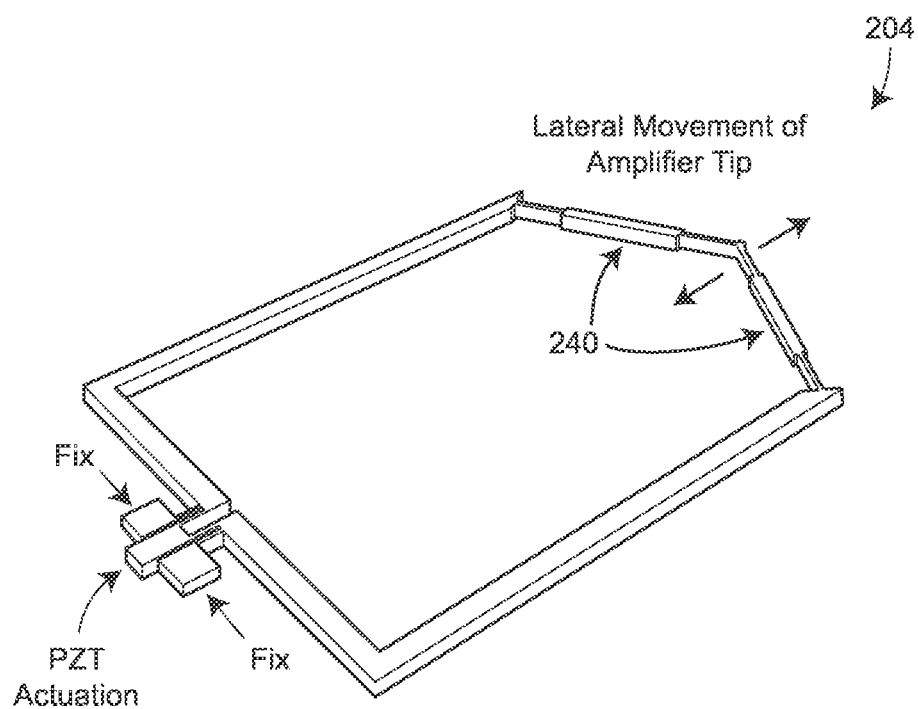

In operation, using the lever-effect the lateral displacement of the piezoelectric plate 208 is transformed into a large transverse displacement of the two lever-beams 225 and 226, in particular at distal outer tips 236 and 238. FIG. 3c illustrates a second portion of the amplification stage 204, in which the transverse movement of the lever beams 226 and 224, specifically the tips 236 and 238, is then re-transformed into a lateral movement of the amplifier-tip using a chevron beam bridge-type amplification structure 240.

Example Modeling of Piezoelectric Lateral to Translational Movement

Figure 4:
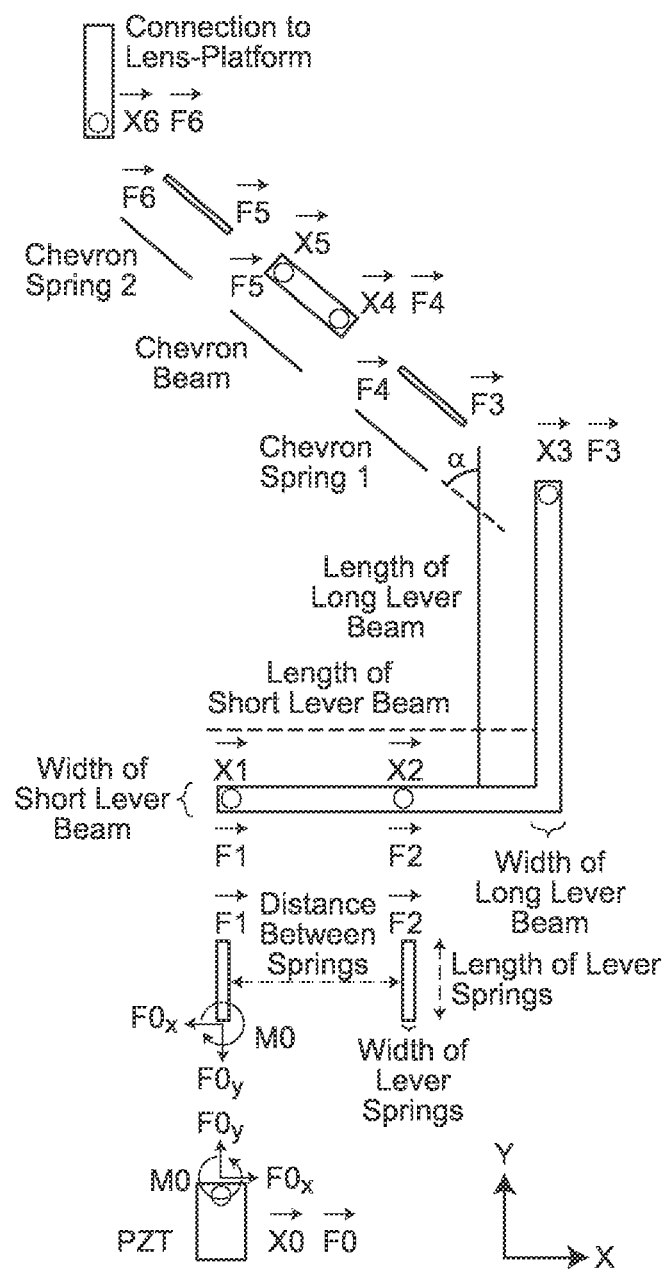
FIG. 4 illustrates a structural segment model of an example implementation of the amplification stage.

For analytical modeling for device optimization a linear mathematical expression was found relating the input of the amplifier to its output taking forces, moments and displacements into consideration, as shown in FIG. 4.

The in-plane deflection and rotation of the i'th flexural element in the design was defined in terms of a stiffness matrix, $K_i$, using linear beam relationships, $$K_i^{-1} = \begin{bmatrix} \frac{L_i^3}{3EI_i} & 0 & -\frac{L_i^2}{2EI_i} \\ 0 & \frac{L_i}{EA_i} & 0 \\ -\frac{L_i^2}{2EI_i} & 0 & \frac{L_i}{EI_i} \end{bmatrix} \quad (1)$$

where $L_i$, $A_i$ and $I_i$ are the i'th flexure's length area and area moment of inertia of the i'th flexure and E is silicon's elastic modulus. Forces and displacements at the flexural elements, $F_i = [F_{x,i} F_{y,i} M_i]^T$ and $X_i = [x_i y_i \theta_i]^T$, respectively, are then $F_1 = K_1(X_1 - X_0)$ $F_2 = K_2 X_2$ $R_1^{-1} F_4 = K_3(R_1^{-1} X_4 - R_1^{-1} X_3)$ $R_2^{-1} F_6 = K_4(R_2^{-1} X_6 - R_2^{-1} X_5)$ \quad (2)

where $R_1$ and $R_2$ are rotation matrices. Geometric relationships for small angular rotations are enforced by a second set of matrix equations, $X_2 = S_{2,1} X_1$ $X_3 = S_{3,1} X_1$ $R_1^{-1} X_5 = S_{5,4} R_1^{-1} X_4$ \quad (3)

where $S_{i,j}$ relates the displacement of two points on the same rigid body to their x- and y-offsets, $L_{x(i,j)}$ and $L_{y(i,j)}$, $$S_{i,j} = \begin{bmatrix} 1 & 0 & L_{y(i,j)} \\ 0 & 1 & L_{x(i,j)} \\ 0 & 0 & 1 \end{bmatrix}. \quad (4)$$

Finally, force balances about each rigid body are completed and written $-F_0 + T_1 F_1 = 0$ $-F_1 + T_2 F_2 + T_3 F_3 = 0$ $-R_1^{-1} F_3 + T_4 R_1^{-1} F_4 = 0$ $-R_1^{-1} F_4 + T_5 R_1^{-1} F_5 = 0$ $-R_2^{-1} F_5 + T_6 R_2^{-1} F_6 = 0$ \quad (5)

where T matrices include small displacement moment arm lengths to perform moment balance calculations.

The system of linear equations provided by Equations (2), (3), and (5) may be solved to relate piezoelectric ceramic force and displacement, $F_0$ and $X_0$, to platform displacement, $X_6$ against a load force, $F_6$.

In particular, x-displacement of the platform, $x_6$, is obtained when transverse and rotational motion of platform and piezoelectric ceramic ($y_6$, $\theta_6$, $y_0$ and $\theta_0$) are constrained to zero by symmetry. In addition, the relationship between the piezoelectric displacement, $x_0$ and the opposing lateral force on the piezoelectric actuator, $F_0$, are related using piezoelectric strain coefficient, $d_{3,1}$, to be $$x_0 = d_{3,1} \frac{V}{t_{PZT}} L_{PZT} + F_0 \frac{L_{PZT}}{E_{PZT} A_{PZT}} \quad (6)$$

where V is applied voltage, $t_{PZT}$, $L_{PZT}$, $A_{PZT}$ and $E_{PZT}$ are thickness, length, cross-sectional area, and elastic modulus of the PZT ceramic.

The full analytical model agreed with finite element models, save for slight over-statement of platform deflection (~10%) due to the neglect of any deformation in the long lever arms. Linear simulations were also compared to nonlinear simulation results, with only small differences. Likewise, stress within the flexural beams was calculated from the intermediate forces in the system equations, again with close agreement to full finite-element simulations, permitting design optimization with maximum stress limits.

Figure 5A:
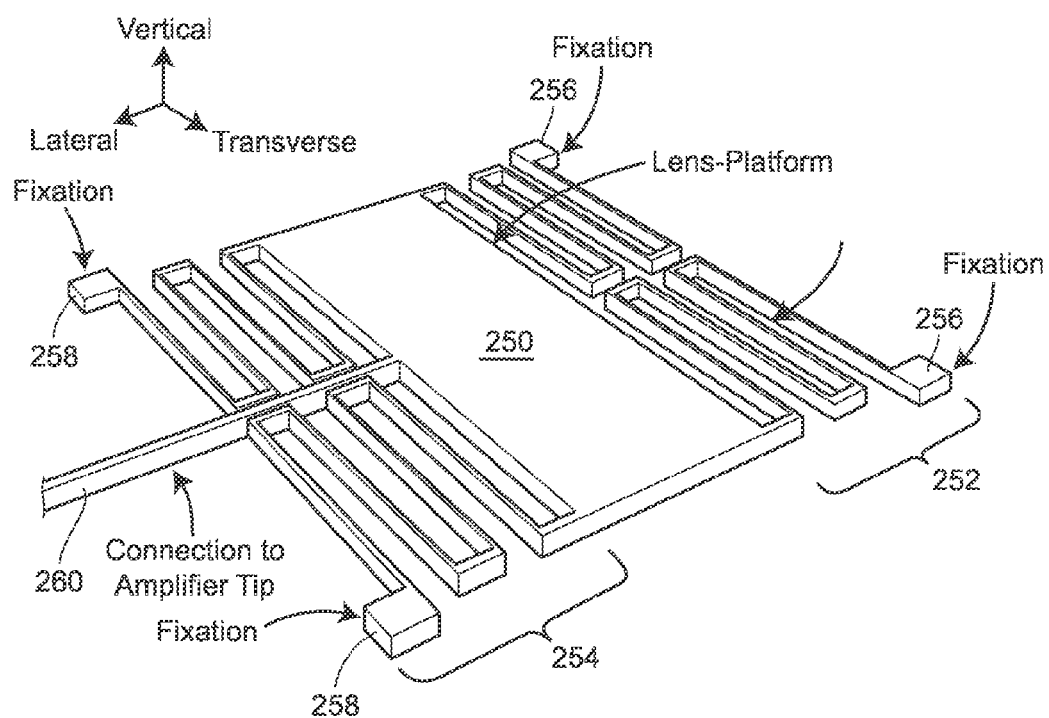
FIGS. 5A-5C illustrate different example implementations of the platform stage of FIG. 2, serving as a lens platform for scanning microscope or endoscope.
Figure 5B:
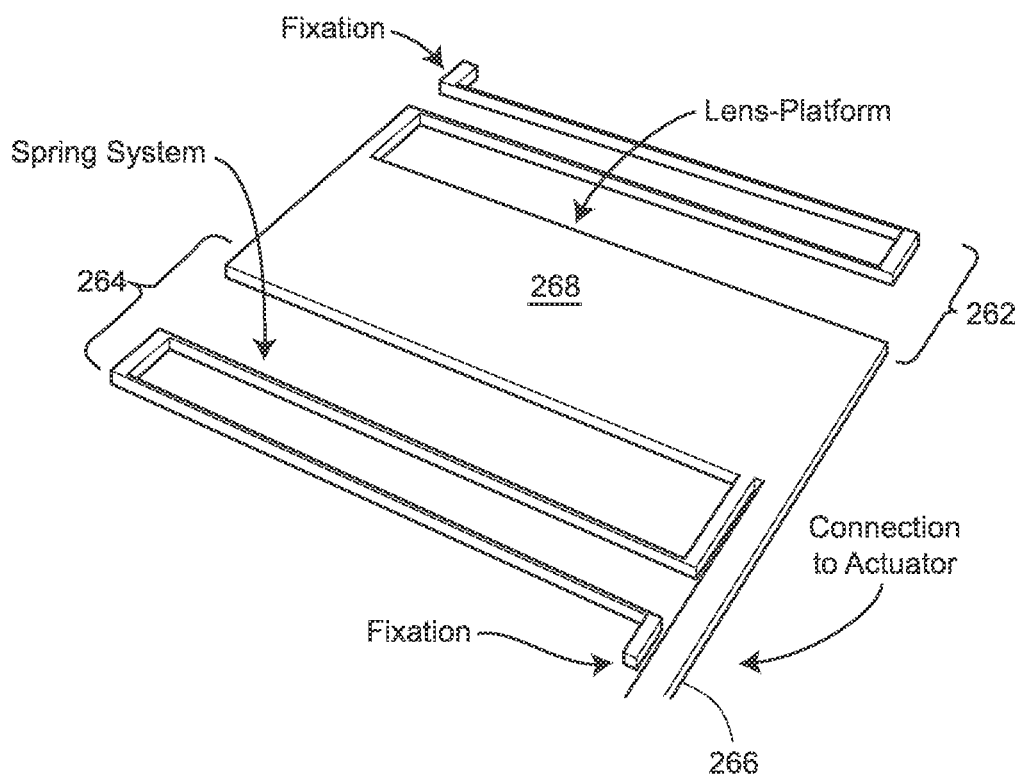
Figure 5C:
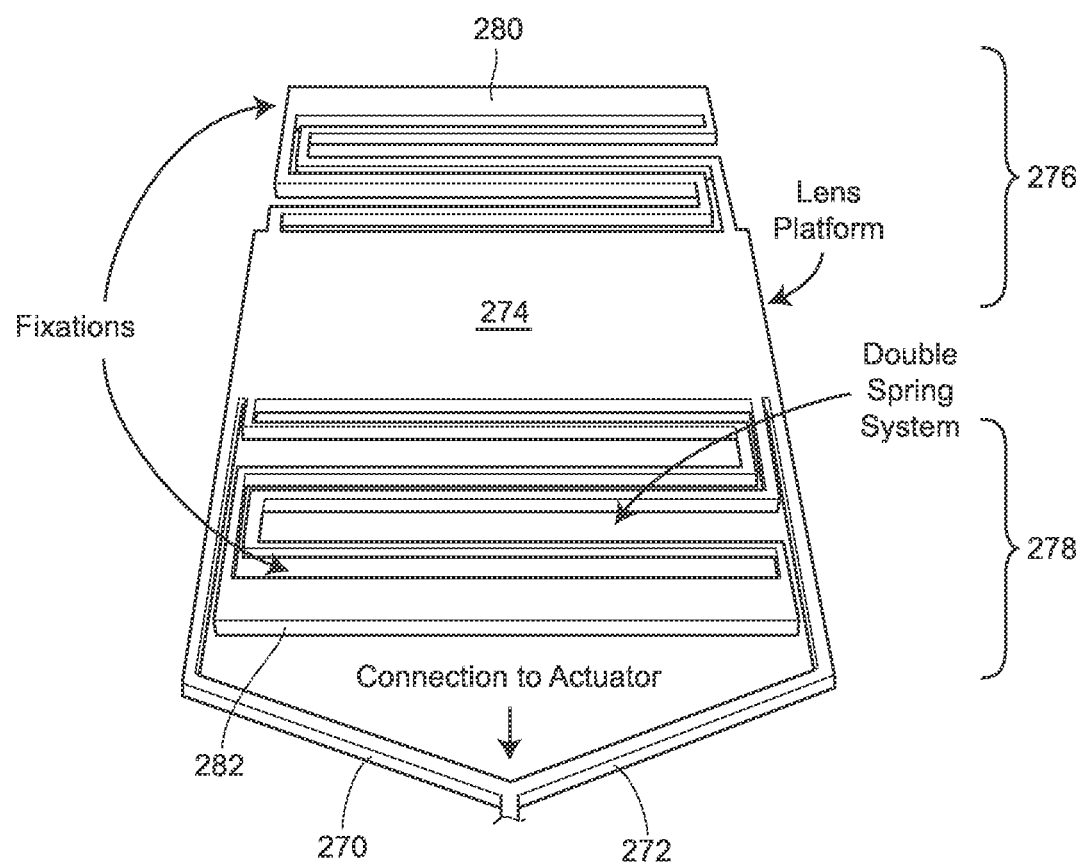

FIG. 5A illustrates an example implementation of the lens platform stage 206 in a suspension design with a lens platform 250 extending between two spring stages 252 and 254 each terminated by fixation bases 256 and 258, respectively. A connection beam 260 bisects spring stage 254 for connecting to the amplification stage 204. FIG. 5B is a similar design, but having fewer meander lines in spring stages 262 and 264, and with a connection beam 266 at an edge of a lens platform 268. FIG. 5C is yet another example design, having chevron beams 270 and 272 connecting to the application stage 204 for moving a lens platform 274 between spring stages 276 and 278, each provided with laterally-extending fixation bases 280 and 282, respectively.

Example Modeling of Suspension Lens Platform

An endoscope application may use two parallel piezoelectric linear actuators to drive the focusing lens resting on the moving platform, where a typical lens mass may be approximately 20 mg. Thus, a suspension platform with a low spring constant in the actuation (lateral or longitudinal) direction and a high spring stiffness in the vertical (transverse) direction is desired. The configuration in FIG. 5A provides a relatively low vertical and transverse spring constant due to the short and meander-shaped spring structures forced by the relatively narrow width of the actuator.

The spring constant k of a set of folded flexures can be given by $$k = \frac{Etw^3}{l^3} \frac{N_{legs}}{N_{folds}} \quad (7)$$

where t is the thickness, w the width and l the length of a single fold of the flexure. To increase transverse and vertical stiffness, additional springs may be added to each link in the folded flexure, forming a double spring system. Lateral stiffness may be kept low by capitalizing on the nonlinear dependence of stiffness on length, with the result that for N times as many springs per link, new length L' need only be increased according to $$l'/l = N^{\frac{1}{3}} \quad (8)$$

to maintain a constant lateral spring constant, all other dimensions being equal. This additional length is accommodated, or even exceeded, by interlacing sets of double springs. FIGS. 5B and 5C show spring layouts for actuators with constrained side-to-side dimensions. The alternate designs use the maximal available length for springs but also providing the platform with a high vertical and transverse spring constant by using a double-spring suspension. Table 2 compares the spring constants and dimensions of the three different suspension systems shown (FIG. 5A—Design 1, FIG. 5B—Design 2, FIG. 5C—Design 3). High transverse and vertical spring constants and high lateral flexibility make FIG. 5C suitable for carrying and guiding a lens that will be fixed perpendicular to the platform's surface.

TABLE 2

|  | Design 1 | Design 2 | Design 3 |
|---|---|---|---|
| $k_l$ | 1.47 N/m | 0.21 N/m | 0.37 N/m |
| $k_t$ | 2.86 N/m | 1.12 N/m | 278 N/m |
| $k_v$ | 9.09 N/m | 7.74 N/m | 25 N/m |
| $k_v/k_l$ | 6.2 | 36 | 68 |
| $k_t/k_l$ | 1.9 | 5.3 | 751 |
| length | 2.56 mm | 2 mm | 4 mm |

Depending on the design, various design parameters may be optimized to achieved the desired translational movement, including suspension lengths and widths and distances between spring connections to the rigid portion of the transmission. An analytical model, with linear simulations and non-linear simulations may be used for optimization. Sweeping the values of single parameters in the analytical model may identify sensitivity to each variable, for example. High influence parameters may then be then analyzed in a Design of Experiments software (JMP) to optimize values when accounting for mutual influences. For example, a non-linear simulation was used to verify the performance of the design in FIG. 2. Table 3 shows key dimensions of a resulting actuator used for experiments (minimum beam width of 8 μm).

TABLE 3

| | |
|---|---|
| lever springs width | 12 μm |
| lever springs length | 100 μm |
| dist. between lever springs | 20 μm |
| short lever beam length | 1200 μm |
| long lever beam length | 4000 μm |
| chevron springs width | 8 μm |
| chevron springs length | 600 μm |
| chevron beam width | 70 μm |
| chevron beam length | 300 μm |
| chevron angle | 60° |
| platform suspension width | 8 μm |
| platform suspension length | 2600 μm |

To fabricate the assembly 200, a Silicon-On-Insulator process was used for the amplifier stage 204 and the platform 214, with a 100 μm thick device-layer and 3 μm thick $SiO_2$ buried oxide layer. First, wafers were coated with Low-pressure chemical-vapor-deposited silicon oxide, for better protection during deep-reactive ion-etching (DRIE), and gold pads were deposited via a lift-off procedure to provide electrical conduction to the underside of the PZT ceramic. The transmission, suspension, and platform geometry was then patterned into the device-layer by DRIE. The backside of the actuators (handle-wafer) was also patterned by DRIE to remove material behind the PZT connection point and the moving platform, reducing the odds of adhesive impeding moving parts. Hydrofluoric Acid (HF) was then used to etch the $SiO_2$ by a timed etch, followed by critical point drying. Minimal surviving feature sizes from the device layer DRIE were 6 μm, used for spring design. Due to long etching times a slight lateral overetching of 1-2 μm and some footing were observed during the DRIE process. The actuator on the wafer was surrounded by an etching trench and automatically detaches from the wafer which replaces dicing. The PZT plate 208 was connected to the handle layer at support 210 and fixed to the movable platform 212 using a silver conductive adhesive.

Experimental results were obtained, for an example implementation, using voltages up to +/−100 V applied to the piezoelectric plate, where the displacement of the amplification and lens platform stages was examined using high speed microscope camera using. At ±100 V DC, a PZT stage displacement of ∓1.43 μm was measured and a platform displacement of ±243 μm was measured, which equaled a total lens platform displacement of 486 μm and an amplification ratio of 170 (all values are DC values). A test was also performed using an AC supply voltage of 3V applied to the electrical contacts of the PZT plate with a frequency swept from 1 to 800 Hz, resulting in displacement for 3V at 10 Hz of 7.5 μm. A distinct resonance frequency was found at 507 Hz with an actuator displacement of 370 μm (no lens included). Although in practice the actuator would likely be operated below resonance, a high resonance frequency is required in order to allow accurate DC-scanning at video frequencies (~10 Hz) when carrying a lens. Experimentally, when a 0.12 g mass was added to a single actuator, natural frequency was measured at greater than 37 Hz, compared to an anticipated 43 Hz.

EXAMPLE

Endoscopic Scanner Design

The present techniques were used to form an optical imaging instrument for the diagnosis and monitoring of inflammatory diseases characterized by eosinophilic infiltration with a focus on allergic rhinitis and eosinophilic esophagitis. The true prevalence of these diseases is unknown and treatment efficacy is difficult to monitor using existing tools for clinical evaluation. For example, in the case of allergic rhinitis, published prevalence rates are highly variable: the disease is largely undiagnosed; they are differing definitions of the condition; and data collections methods can vary. Current estimates suggest that more than 50 million people in the United States suffer from allergic rhinitis. In one study, 42% of children had physician-diagnosed allergic rhinitis by 6 years of age. Moreover, allergic disorders are estimated to affect some 1.4 billion people globally, and there appears to be a worldwide epidemic of allergic diseases. Studies suggest this is likely a consequence of our changing environment, reduced infections, and genetic susceptibilities.

Eosinophilic esophagitis (EoE) is a relatively new disease with about a 10-fold increase in prevalence over the past 20 years. It has been found in approximately 6.5% of the population undergoing upper endoscopy and has become one of the leading causes of dysphagia and food impaction in adults. For diagnosis, endoscopy is performed and multiple biopsies are collected at random throughout the length of the esophagus, including the proximal and distal regions. On histopathology, the primary feature of EoE is infiltration of eosinophils into the mucosa. These mediators of inflammation may contribute to the development of structural abnormalities of the esophagus, including edema, rings, furrows, and strictures. Clinical symptoms do not improve with high-dose proton pump inhibitor therapy, and the pH in distal esophagus is usually normal. However, the diagnostic criteria for this disease seem to lack clarity. EoE may be difficult to distinguish from gastroesophageal reflux disease (GERD), which is also associated with increased eosinophilia, but to a lesser extent. The two diseases may be present at the same time. Eosinophils can also trigger allergic symptoms in other parts of the gastrointestinal tract.

Another issue with diagnosis is that the degree of mucosal hypereosinophilia that defines EoE is fully established. Although a diagnostic criteria of ≥5 eosinophils per high-power field (hpf) on histology has been proposed, values as high as 30 eosinophils per hpf have been used; and no single number is widely accepted. Diagnostic uncertainty for this disease may be attributed in part to its patchy and focal nature. In addition, little is known about the density or spatial distribution of eosinophils throughout the mucosa. Marked variability has been found within and between biopsy specimens of individual patients, resulting in a low sensitivity for detection. Currently, biopsy specimens are sectioned along a plane whose orientation to the mucosal surface is unknown. A non-uniform distribution of infiltrating eosinophils within the mucosa could result in a highly variable cell count that depends on the angle of sectioning, resulting in an inaccurate result. The techniques, herein, however, provided a method for quickly and reliably quantifying the number of cells over a 3D volume space overcoming this tissue processing limitation.

Human eosinophils contain granules that produce an intense autofluorescence in comparison with the surrounding squamous epithelium. There is evidence to support flavin adenine dinucleotide (FAD) as the source of this endogenous fluorescence. FAD is a coenzyme in the mitochondrial electron transport chain that has a maximum absorption at 445 nm, resulting in a peak fluorescence emission of 525 nm. The multi-photon microscopy techniques described herein were used to collect fluorescence images from cells and tissues and to perform in vivo imaging of FAD from squamous epithelium in animals.

For example, by utilizing the techniques herein to produce a miniature, fiber-coupled multi-photon (e.g., two-photon) instrument with form factor compatible with endoscopic as well as handheld use, multi-photon microscopy could be applied to the diagnosis and monitoring of these and other diseases. These include diseases where eosinophilic infiltration contributes to the pathophysiology of the disease. In addition to allergic rhinitis and eosinophilic esophagitis, other entities such as asthma, connective tissue disorders, and certain cancers can present with increased eosinophilia.

Figure 6:
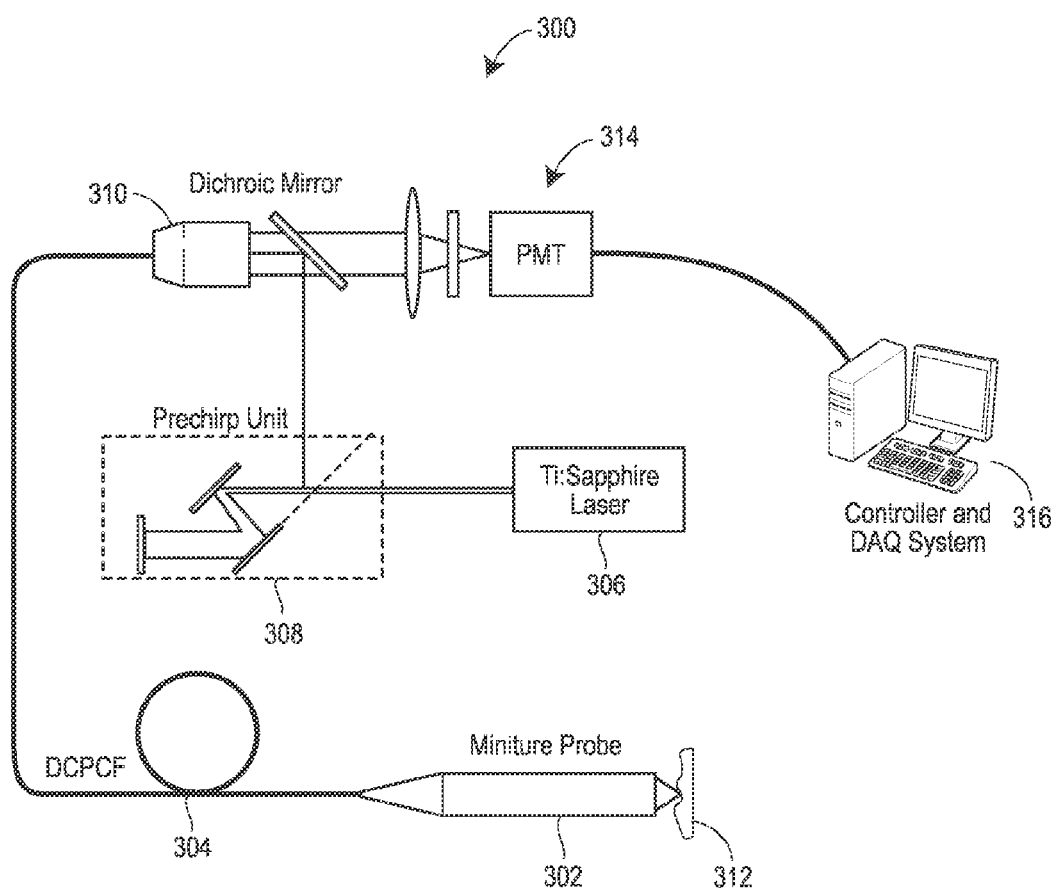
FIG. 6 illustrates a diagnostic system employing a 3D scanning optical instrument for image pick up, in accordance with an example.

FIG. 6 illustrates a diagnostic system 300 that utilizes a miniature multi-photon microscopy optical instrument—in this example a two-photon imaging endoscope 302 with three-axis scanning as discussed above—for quantitative detection of tissue eosinophils as a biomarker of inflammation in studies on allergic rhinitis and eosinophilic esophagitis. The endoscope 302 is coupled to a double-clad optical fiber 304 receiving a laser energy from a Ti:Sapphire Laser stage 306 feeding a prechirp unit stage 308 that corrects for phase dispersion broadening of the optical fiber 304 and that is coupled to coupling/decoupling lens stage 310. The laser energy coupled to the endoscope 302 is a feed energy used to produce a resultant two-photon excitation fluorescence that can be used to distinguish between eosinophils and epithelial cells on human nasal cytology tissue 312. That resulting excited fluorescence is captured by the endoscope 302 and coupled back into the fiber 304 and decoupled by the lens element 310 into a 2D fluorescent imaging stage, or photomultiplier stage 314.

To control operation of endoscope 302, in particular the piezoelectric induced z-axis scanning and the xy-scanning of an internal xy scanning stage, the endoscope 302 is electrically coupled to a remote control system 316, having a processor, input device, communications interface, and a display. In the illustrate example, the control system 316 is also coupled to the imaging stage 314 for collecting imaging data for display at the control system 316.

Example 1

Figure 8:
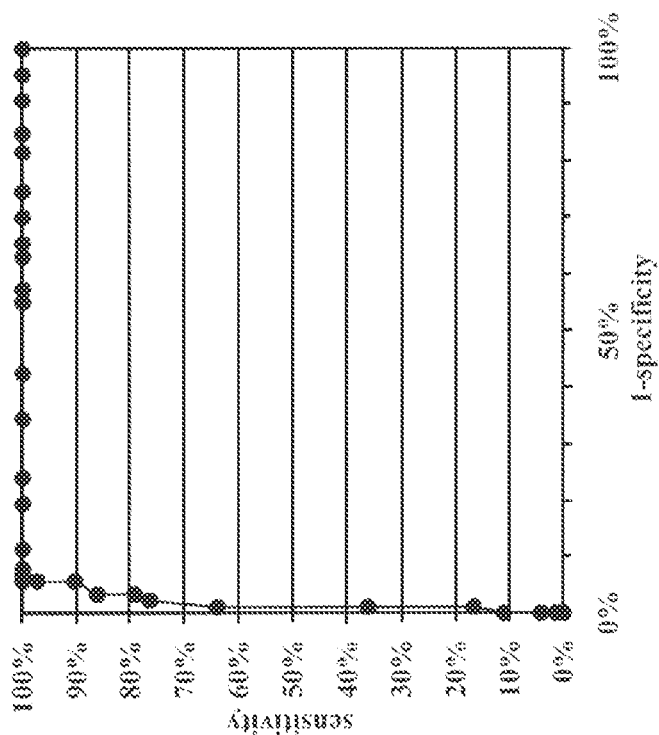
FIG. 8 is a plot of sensitivity versus sensitivity versus specificity at various threshold intensities for a two-photon excited fluorescence collected using the system of FIG. 6 to distinguish eosinophils from epithelial cells.
Figure 7:
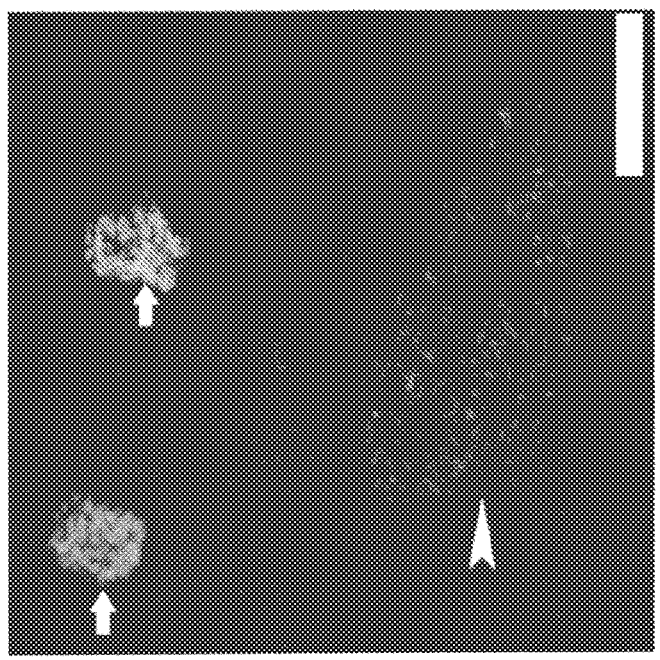
FIG. 7 is a fluorescence 2D image of emission collected between 500 nm and 600 nm of a biologic sample (bilateral nasal smears) imaged in accordance with an example.

In a first example implementation, bilateral nasal smears were performed on 30 human subjects with rhinitis symptoms, and imaged with a laboratory two-photon microscope with 162.5 mW excitation at 700 nm wavelength. Fluorescent images (see, e.g., FIG. 7) for emission between 500 and 600 nm were taken and compared to histology. A significantly greater mean fluorescence intensity was observed from eosinophils compared to epithelial cells, 13.8±4.3 versus 3.7±1.8 ($p<0.01$), respectively. A receiver operator curve (ROC) is shown in FIG. 8 presenting the sensitivity versus specificity at various threshold intensities for use of a two-photon excited fluorescence to distinguish eosinophils from epithelial cells, resulting in an area under the curve of 98%.

Figure 9:
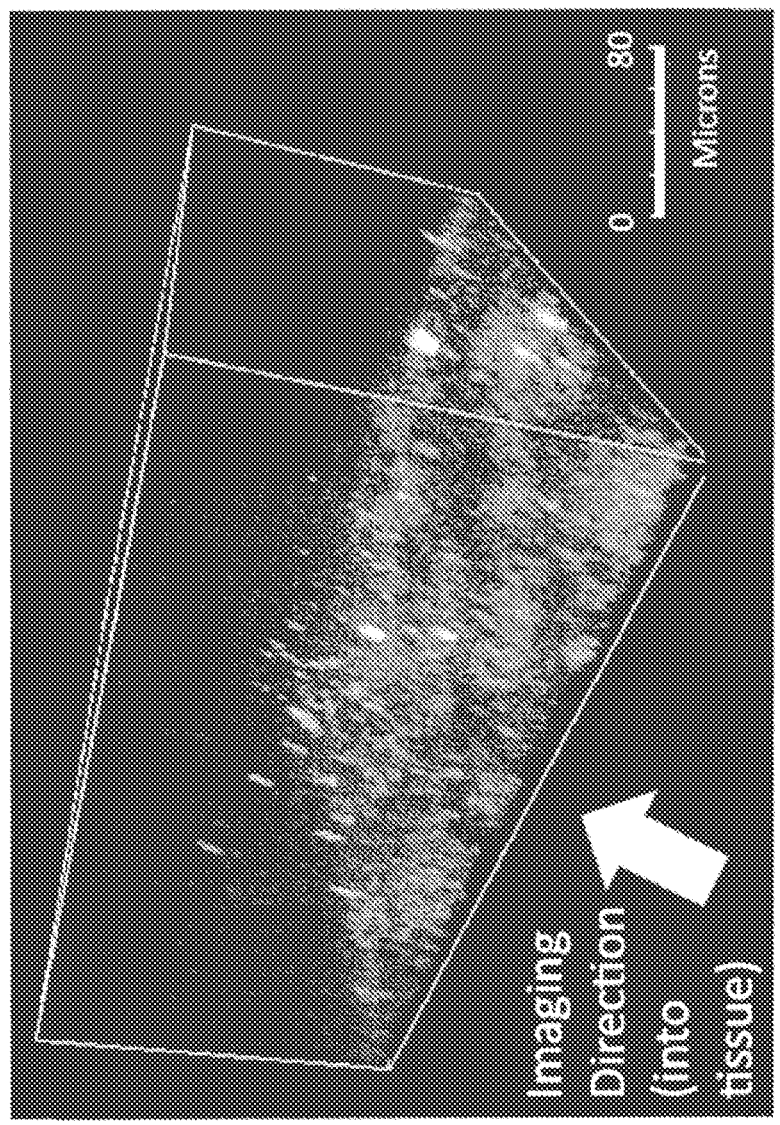
FIG. 9 is a 3D volumetric image of eosinophils in esophageal mucosa, as obtained using the system of FIG. 6.

Using volume scanning (z-axis and xy-plane scanning), the present techniques were able to use the two-photon fluorescence technique to establish 3D volumetric imaging of eosinophils in esophageal mucosa, as shown in FIG. 9. In an example, a endoscope having a field of view of 228 µm×228 µm×113 µm was used to perform 40 section images, each imaged at 2.9 µm increment steps (in the z-axis), to image the spatial distribution of the eosinophils. This initial empirical data was obtained using a two-photon scanning system capable of achieving displacements of 90 to 120 µm using bulk and thin-film piezoelectric (PZT ceramics) materials. For even further depth penetration (i.e., displacements of 450 µm or greater), configurations such as those in FIGS. 1-5 may be used instead.

Figure 10A:
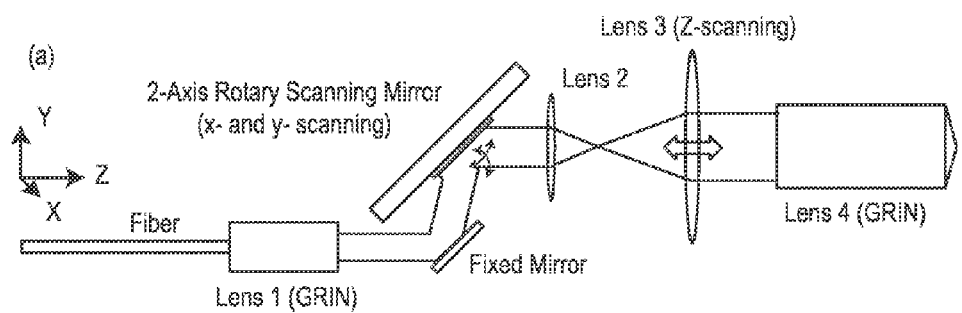
FIG. 10A illustrates a top view of a schematic illustration of a 3D scanning optical instrument.
Figure 10B:
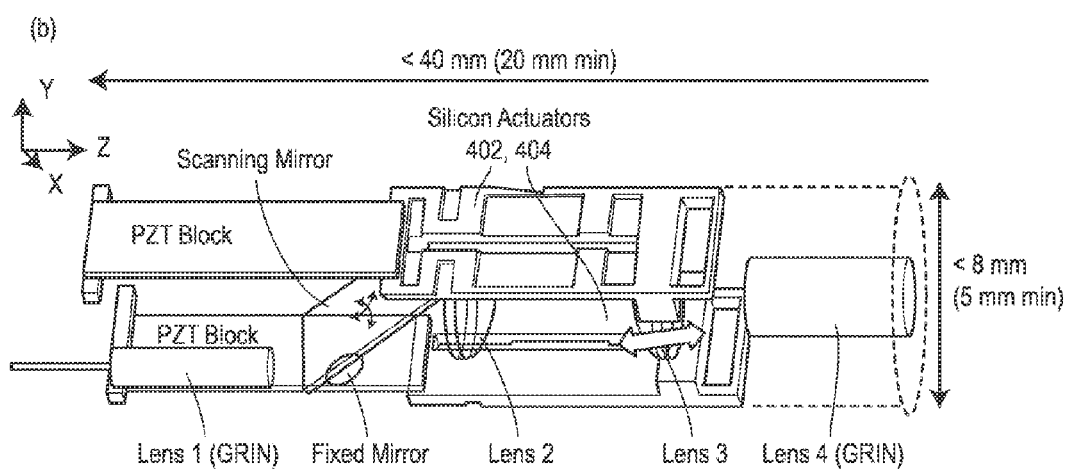
FIG. 10B illustrates a perspective view of microactuation portion of the illustration in FIG. 10A.
Figure 11A:
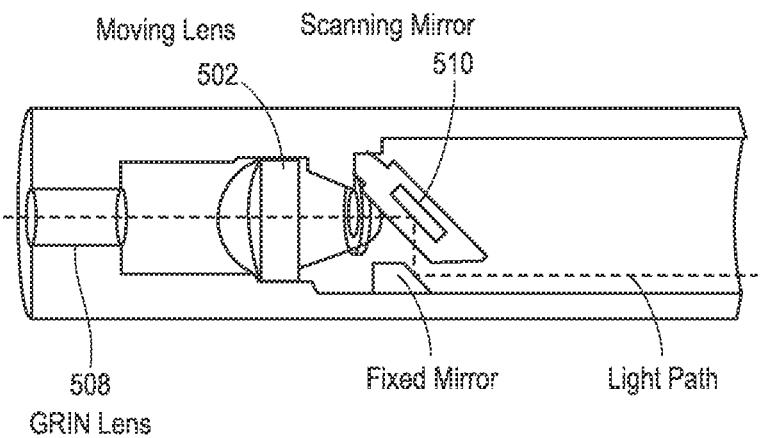
FIGS. 11A and 11B illustrate partial cross-sectional views and an internal solid model view of an assembled endoscopic device having 3D scanning capabilities.
Figure 11B:
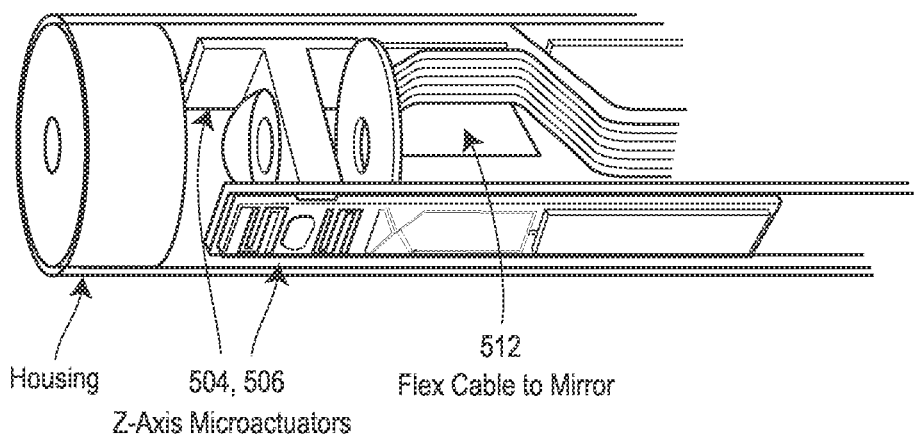

By way of example, a high-speed 3-axis scanning endoscope design 400 (FIG. 10A) used in a hand-held compatible form factor, with a scanning head in a 5 mm diameter package, compatible with an Olympus XT-100 upper endoscope that has a 6 mm diameter instrument channel. FIG. 10A illustrates a schematic view of 3-axis scanning, while FIG. 10B illustrates a schematic rendition thereof using PZT based microactuators, having silicon substrates. The laser stage was a femtosecond pulse laser coupled through from a 1 mm GRIN lens collimator to a two-axis, aluminum-coated scanning silicon MEMS mirror via a smaller fixed mirror. The scanning mirror was a commercial design by Mirrorcle Technologies, Inc. (Albany, Calif.), providing a +/−10° optical scan angle at frequencies of at least 3000 Hz. A pair of aspherical lenses magnified the light path following scanning mirror, to provide sufficient numerical aperture at the tissue surface, through a 1.8 mm GRIN focusing lens. To perform z-axis (into tissue) scanning, Lens 3 (the second aspherical lens) was translated by piezoelectric microactuators 402 and 404, adding a unique capability to the proposed system. FIG. 11A illustrates a partial cross-sectional view of a model of the assembled device; and FIG. 11B illustrates an internal view an assembled endoscope 500 with 3D scanning capability. A moving lens assembly 502 is coupled to microactuator scanning stages 504 and 506 for z-axis scanning through a GRIN lens 508, while a scanning mirror 510 provides xy-plane scanning. In the illustrated example, control signals for scanning are provided by a flex cable 512.

The performance of the optical design was verified through analytical calculations and optical simulation with ZEMAX optical modeling software. Analysis results indicate that scanning ranges of at least 300 μm in each of the three scanning dimensions are possible, with optimal spherical lenses of NA 0.55 and 0.6.

Example 2

In another study, patients aged 18-65 years who are undergoing routine endoscopy and have symptoms consistent with EoE, including dysphagia or food impaction were recruited for an endoscopic imaging analysis. Patients were excluded if they had a known bleeding disorder or an elevated International Normalized Ratio (>1.5) owing to anticoagulation. Patients with severe illness such as heart failure, difficulty breathing, or kidney failure were also excluded. A total of 23 patients were recruited into this study with ages ranging from 21 to 64 years old (mean 42±13), including 12 females and 11 males. The patient demographics, symptoms on presentation, therapy before the study, and cell count on multi-photon microscopy and histopathology are presented in Table 4.

After completion of the routine portion of the endoscopy for each patient, additional specimens were collected for research purposes. A total of 4 biopsies were obtained: 2 from the proximal esophagus (~20-30 cm from the gums) and 2 from the distal esophagus (~2 cm above the Z-line). The specimens were placed immediately into separate vials containing normal saline, and transferred on ice to the laboratory microscope for imaging. The specimens were placed individually with the luminal side of the mucosa facing downward onto the surface of a #1.5 cover glass in a chamber slide. A small amount of normal saline was used to keep the specimens moist during imaging. Fluorescence images were collected from all specimens within 4 hours of resection.

After imaging, the specimens were prepared for pathologic evaluation. Specimens were placed in Eppendorf tubes containing 5 mL of formalin and kept overnight for fixation. The following day, the specimens were immersed in 70% ethanol, cut in 5-μm sections, and stained with hematoxylin and eosin for routine histopathology. The remaining portions of the specimens were paraffin embedded and stored.

The specimens were imaged using a multi-photon microscopy scanning endoscope in accordance with the present techniques. A tunable, ultrafast laser producing a 100-femtosecond pulse width (Spectra-Physics, Mai Tai HP) was employed to provide the photon excitation source. A multi-photon excitation at 700 nm was used on cultured cells and human eosinophils; and fluorescence was collected between 500 and 600 nm. Both 2D and 3D images were obtained from each specimen, using a scanning control system like that of 300 shown in FIG. 6. To achieve a large field of view (FOV) with deep tissue penetration, a 20× objective with a numerical aperture of 0.70 and working distance of 0.59 mm was used as the lens stage. Images were collected with an FOV of 775× 775 μm$^2$ from 0 to 200 μm in axial depth. The settings for the laser and the detectors were kept constant for all specimens.

Immunohistochemistry was performed to validate the source of the fluorescence. Frozen sections were fixed with 1% paraformaldehyde/phosphate-buffered saline, and then blocked with 20% fetal bovine serum/phosphate-buffered saline for 1 hour at room temperature. Sections were then incubated with mouse anti-EPO primary antibody (clone AHE-1; Chemicon, Billerica, Mass.) in blocking solution (1:100 dilution) at 4° C. overnight. This antibody reacts specifically with the human eosinophil peroxidase, an enzyme that plays an important role in endothelial injury in hypereosinophilic states. The specimens were then labeled with Alexa Fluor-594 conjugated goat anti-mouse secondary antibody (Invitrogen, Carlsbad, Calif.) and mounted with Pro-Long Gold anti-fade reagent (with DAPI; Invitrogen).

Images from the multi-photon microscopy scanning assembly were evaluated by using the "analyze and measure" command in Image J software (National Institutes of Health,

TABLE 4

| Age | Gender | Presenting Symptoms | Therapy | Multiphoton Absolute Eos# | Pathology Max Eos# |
|---|---|---|---|---|---|
| 60 | F | Dysphagia | Omeprazole 40 mg bid | Distal-13 | Distal-7 |
| 42 | M | H/o impaction, stricture, dilation | Omeprazole 20 mg prn | NA | NA |
| 36 | M | Dysphagia, food impaction | Omeprazole 20 mg qd | NA | NA |
| 52 | F | EoE on Flovent, dilation q3-4 mo | None | Distal-13 | Distal-5 |
| 33 | M | Dysphagia | Omeprazole 20 mg bid, ranitidine 150 mg bid | 0 | 0 |
| 53 | F | GERD-like | Omeprazole 20 mg bid | 0 | 0 |
| 60 | M | H/o Barretts, suspected EoE | Omeprazole 20 mg qd | Proximal-8, distal-12 | 0 |
| 56 | F | GERD-like | Ranitidine 150 mg prn | Proximal-14 | 0 |
| 64 | F | GERD-like, family h/o EoE | None | 0 | 0 |
| 33 | F | New diagnosis of EoE | Omeprazole 20 mg bid | Proximal-21, distal-20 | Proximal-16, distal 5 |
| 34 | M | New diagnosis of EoE | Omeprazole 20 mg bid | Proximal-7, distal-15 | Proximal-4, distal-13 |
| 21 | M | Dysphagia | None | 0 | 0 |
| 25 | M | H/o EoE, GERD-like, dysphagia | Omeprazole 20 mg bid | Proximal-175 | 2 |
| 33 | M | H/o EoE | Pantoprazole 40 mg qd | Proximal-5 | 0 |
| 24 | F | GERD-like | Omeprazole 20 mg qd | 0 | 0 |
| 43 | M | EoE, dysphagia | Omeprazole 40 mg qd | Distal-56 | Proximal-4, distal-29 |
| 26 | F | Dysphagia | Lansoprazole 30 mg qd | Proximal-4, distal-12 | 0 |
| 59 | F | Dysphagia, GERD-like | Omeprazole 40 mg qd | Distal-11 | 0 |
| 49 | F | GERD-like | Omeprazole 20 mg bid | Proximal-2, distal-5 | Distal-1 |
| 41 | F | Chest pain, GERD-like | Omeprazole 20 mg qd | Distal-18 | Distal-16 |
| 43 | M | Dysphagia, food impaction | None | Proximal-159, distal-31 | Proximal, distal-66 |
| 57 | F | Dysphagia | None | Proximal-6, distal-110 | Distal-4 |
| 42 | M | Dysphagia | None | Proximal-1, distal-10 | Distal-2 |

Bethesda, Md.). Eosinophils were identified based on characteristics of fluorescent intensity, cell size, and cell shape. Cells that had dimensions ranging between 7 and 15 µm were included in the analysis. The mean and standard deviation of the fluorescence intensity of each cell and the surrounding squamous epithelium were measured. In addition, the size of each cell was recorded. Measurements were taken from 4 eosinophils and equivalent regions of epithelium in each specimen, if available. The maximum number of eosinophils per hpf were counted on the histology on viewing at 40× magnification. In addition, the absolute number of eosinophils on the resulting images were counted and compared with that found on histology. The images were then generated using AutoQuant×2 (Media Cybernetics, Inc, Bethesda, Md.) software. Vertical cross-sectional images were then obtained by taking a projection of the 3D image perpendicular to mucosal surface. An exponential fit of the average number of eosinophils versus mucosal depth was calculated using OriginPro 8.1 (OriginLab Corp., Northampton, Mass.).

The histology was reviewed by a gastrointestinal pathologist (HA) who was blinded to the results of the images. The pathologist reported if eosinophils were present, and if so, quantified the maximum number of eosinophils per hpf.

Statistical significance (P-value) was calculated using the 2-sided Student t-test with unequal variance. All results are shown as mean values±standard deviations. The relationship between eosinophil count on the images and pathology evaluation was compared using linear regression. Statistical analysis was performed using the data analysis package in Microsoft Excel 2007.

Figure 12A:
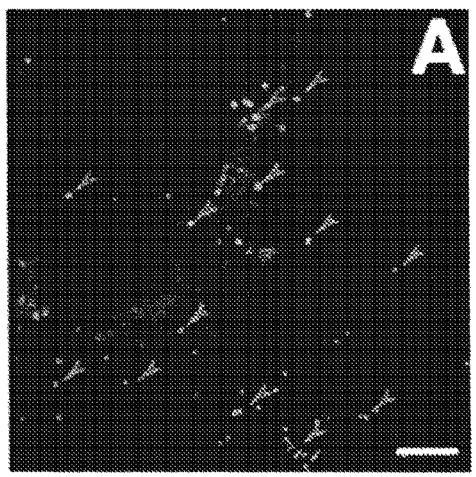
FIG. 12A-12F are images of esophageal mucosa collected in horizontal cross-sections using a multi-photon microscopy scanning assembly.
Figure 12B:
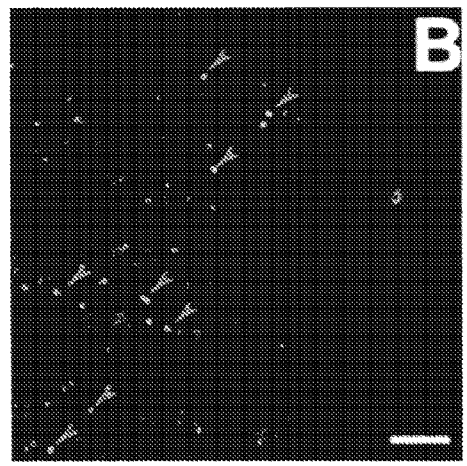
Figure 12C:
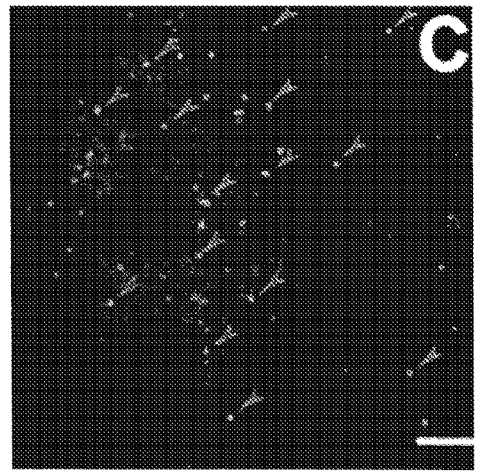
Figure 12D:
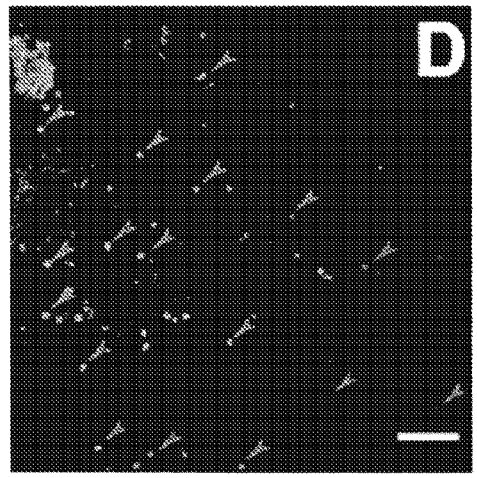
Figure 12E:
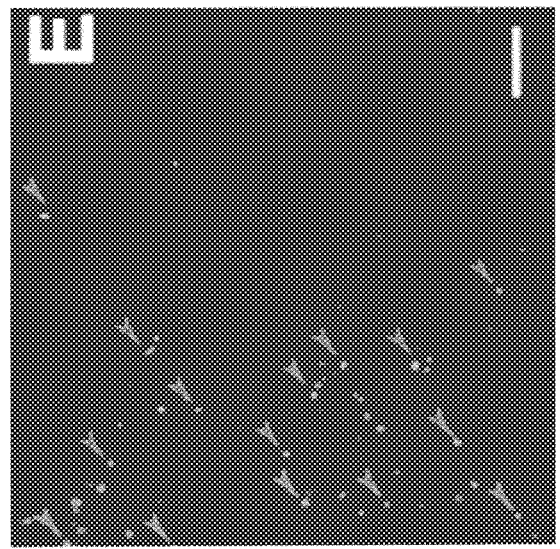
Figure 12F:
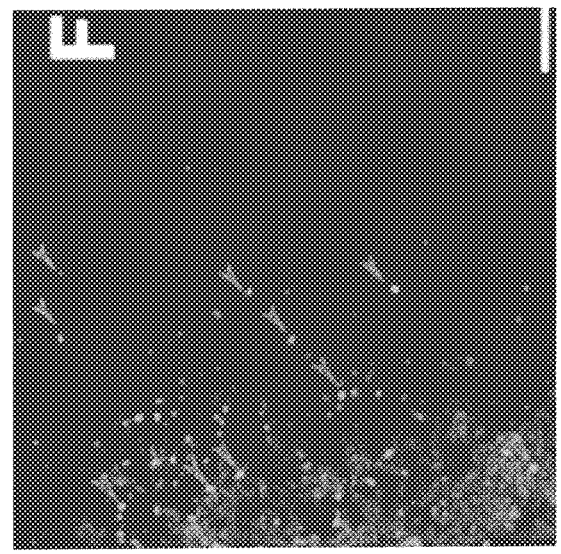
Figure 12G:
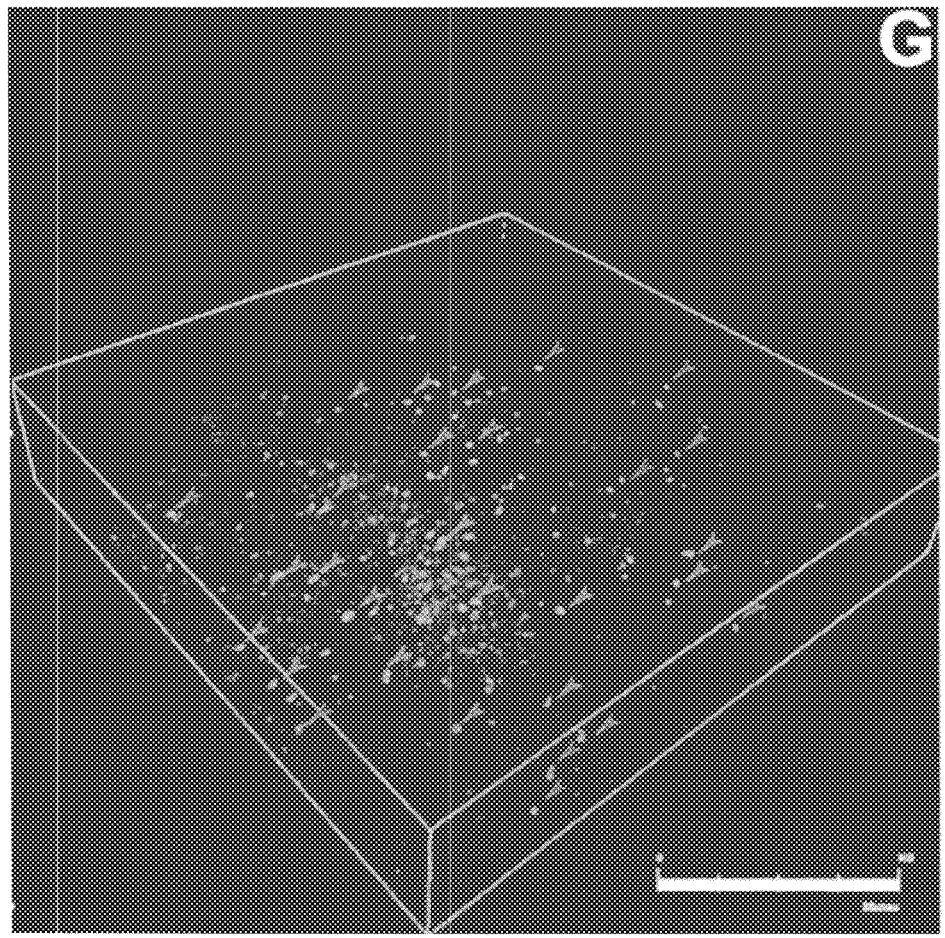
FIG. 12G is an image of a resulting 3D volume rendered image formed from the images of FIGS. 12A-12F.

Based on routine histopathologic review, eosinophils were found on 11 specimens. On the resultant images, eosinophils were found on the same 11 specimens as well as on 5 additional specimens. FIGS. 12A-12F provide images of esophageal mucosa collected in horizontal cross-sections (FOV 775×775 µm$^2$) using the a multi-photon microscopy scanning assembly. The images show punctate regions of bright fluorescence from eosinophils (see arrows) infiltrating squamous epithelium, characterized by a diffuse and much dimmer pattern of fluorescence from the epithelium. Images are collected from the mucosal surface (d=0 µm) and increase with depth in 20-µm increments (scale bar, 100 µm). In FIG. 12G, e.g., the resulting 3D volume rendered image, formed by the control system 316, shows the distribution of eosinophils within the mucosa (scale bar, 400 µm). We were able to accurately identify and quantify the eosinophils on these images using fresh, unstained, unfixed specimen, and observed significantly greater mean two-photon microscopy intensity from the eosinophils in comparison to the surrounding epithelium. The average target-to-background ratio on the EoE positive images from a depth of d=0 to 50 µm is 4.47±4.34 (range, 1.38-31.14) and from d=51 to 200 µm is 3.87±2.76 (range, 1.94-15.59; P=0.01).

Figure 12H:
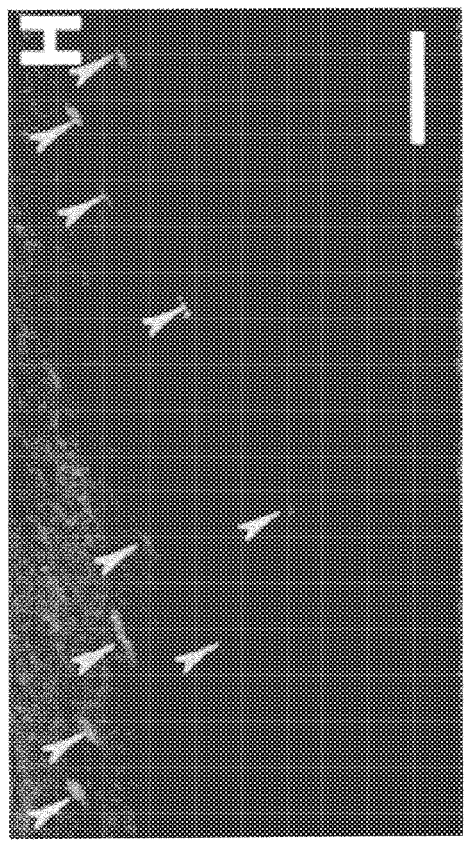
FIGS. 12H-12I are images identifying eosinophils.
Figure 12J:
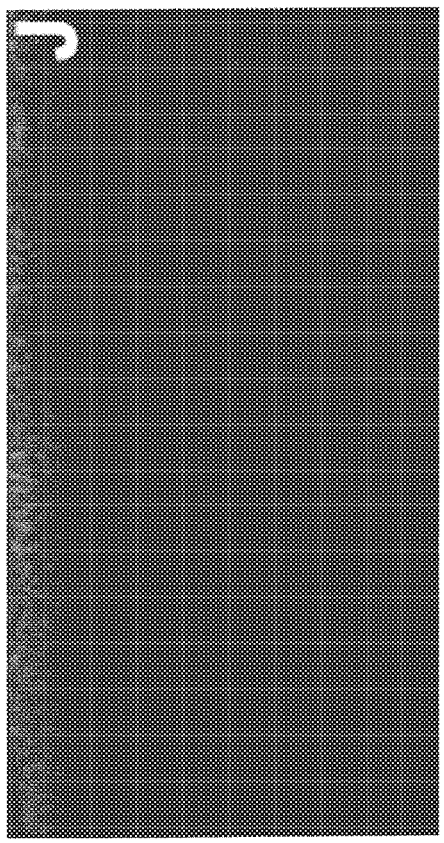
FIGS. 12J-12K show no infiltrating eosinophils in the esophageal mucosa.
Figure 12I:
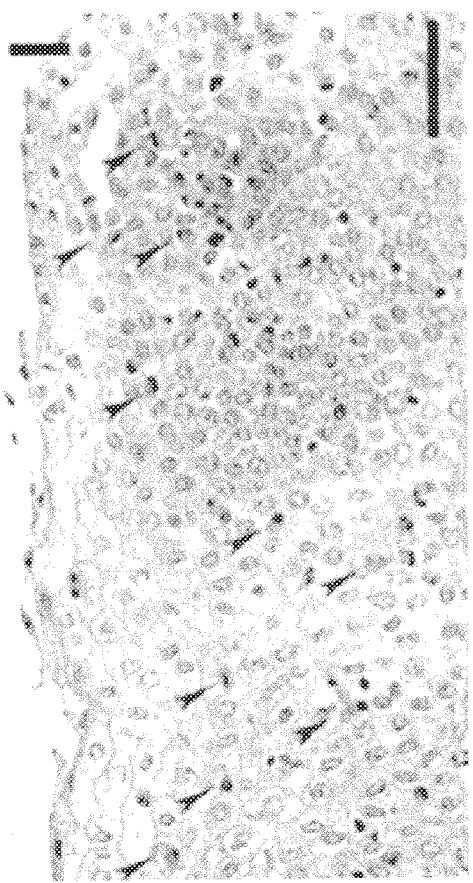
Figure 12K:
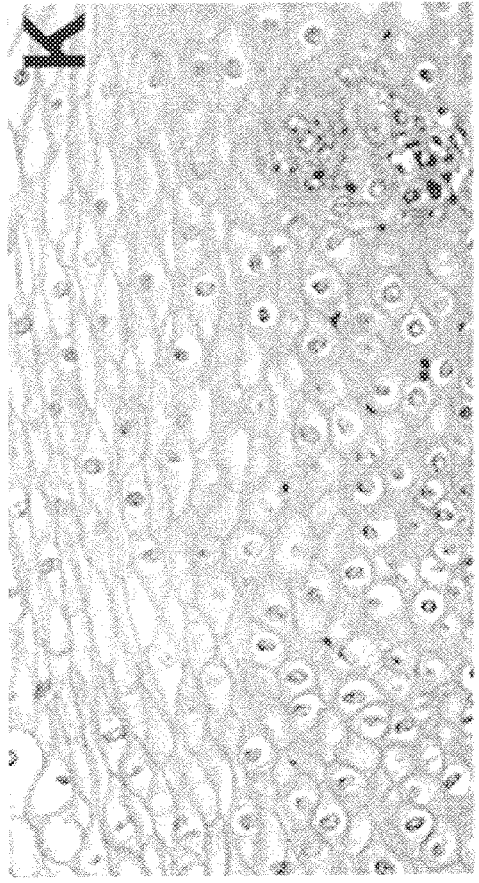

Vertical cross-sectional images (perpendicular to mucosal surface) show the distribution eosinophils with mucosal depth. These images are generated from the 3D volumetric images shown above. In FIG. 12H, several eosinophils (see arrows) can be identified from the punctate regions of increased fluorescence intensity compared with that of the surrounding squamous epithelium (scale bar, 25 µm). The oval shape of the eosinophils result from processing performed to generate the vertical cross-sectional images. The corresponding histology (stain: hematoxylin and eosin) in FIG. 12I confirms the presence of eosinophils (see arrows). By comparison, a vertical cross-sectional image from a specimen of esophageal mucosa collected from a patient with no infiltrating eosinophils is shown in FIG. 12J as a control. The corresponding histology (stain: hematoxylin and eosin) shown in FIG. 12K confirms the absence of eosinophils.

Figure 12L:
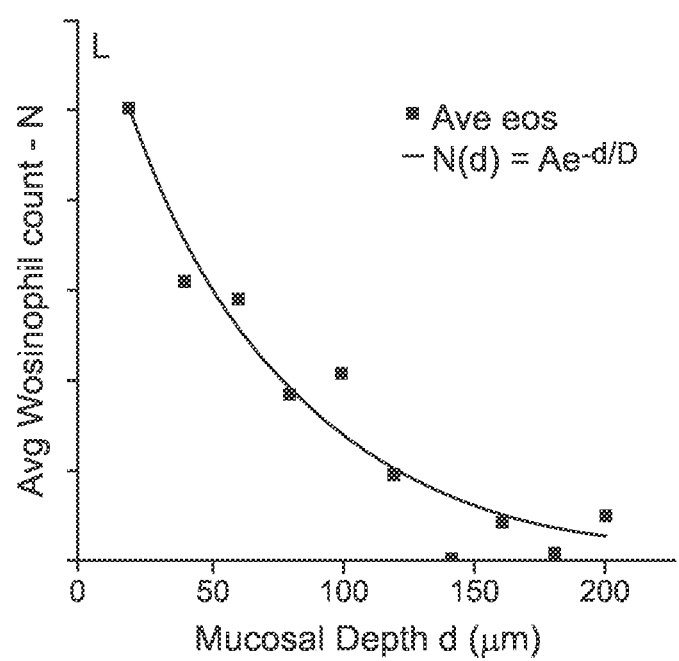
FIG. 12L is a plot of the average number of eosinophils at different depths below the mucosal surface.

The average number of eosinophils on the positive specimens at different depths below the mucosal surface was found from the vertical cross-sectional images, and is shown in FIG. 12L. The concentration of eosinophils seems to be highest near the mucosal surface, and decreases in approximately an exponential fashion with tissue depth down to approximately 200 µm. A fit of the average number of eosinophils as a function of depth to the equation $n(D)=Ae^{-d/D}$, resulted in values of A=17 and D=62.5 µm. We found that, on the a multi-photon microscopy images, 96% of the eosinophils present within the esophageal mucosa can be found within a 200-µm-thick layer below the surface. A direct comparison of eosinophil count versus depth on histology was limited by artifacts introduced by specimen processing.

Figure 13A:
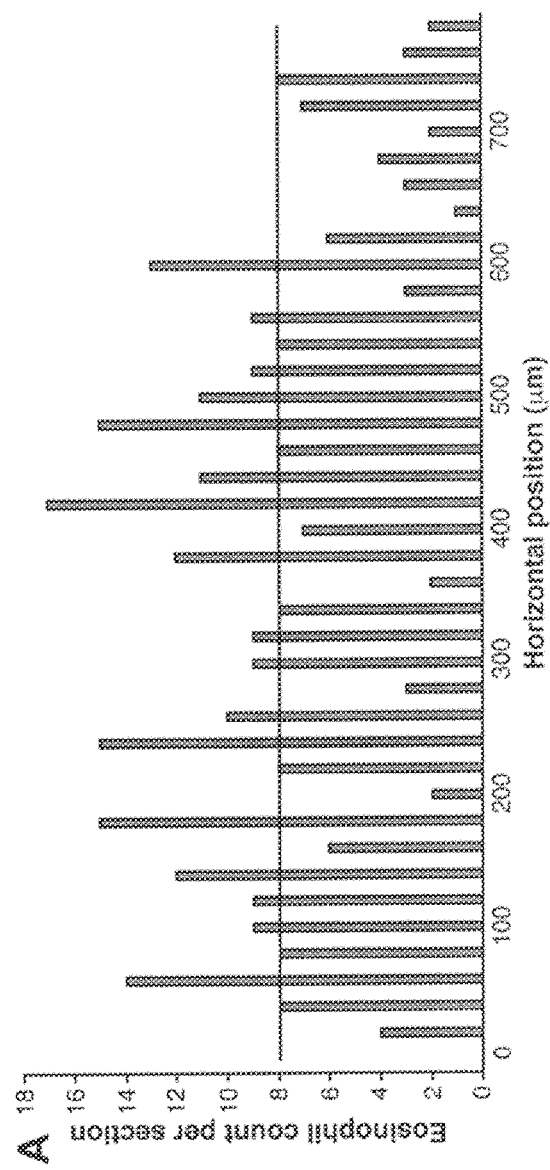
FIG. 13A is a graph showing the number of eosinophils found on individual vertical cross-sectional multi-photon microscopy images in horizontal increments of 20 µm across the mucosal surface of the esophageal specimen.

In FIG. 13A, the number of eosinophils found on individual vertical cross-sectional two-photon microscopy images with dimensions 775 µm wide by 200 µm deep is shown in horizontal increments of 20 µm across the mucosal surface of the esophageal specimen. The numbers ranged from 1 to 17 cells with an average of 7.95±4.24 (horizontal line). This result shows that any single section is unlikely to accurately represent the average number of cells over the volume of the specimen.

Figure 13D:
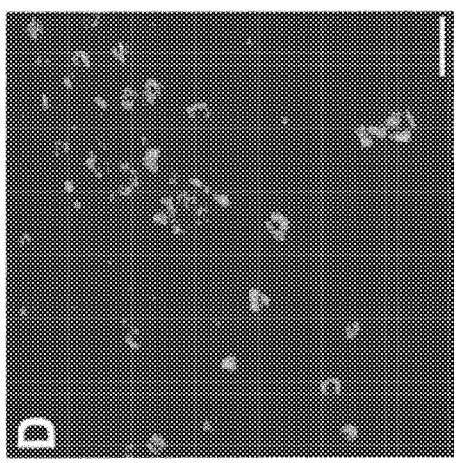
FIGS. 13B-13D are images of discrete foci of bright fluorescence microscopy images taken in horizontal cross-sectional images of superficial squamous epithelium (FIG. 13B), immunohistochemistry images of serial section of epithelium stained with the anti-EPO antibodies (FIG. 13C), and an overlay of the two images, registered, and confirming eosinophils as the source of the bright fluorescence (FIG. 13D).
Figure 13C:
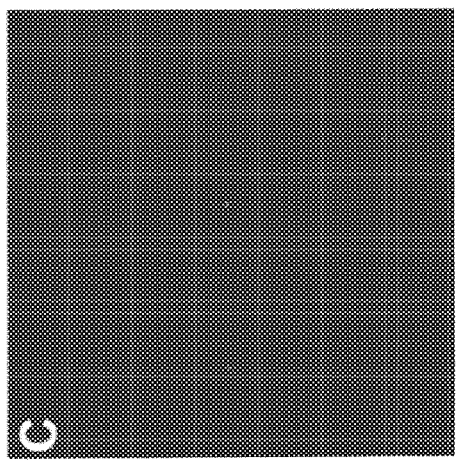
Figure 13B:
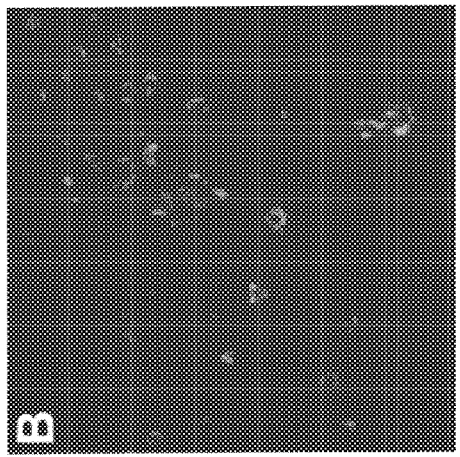

Immunohistochemistry was performed to validate the source of the a multi-photon microscopy image. In FIG. 13B, numerous discrete foci of bright (green) fluorescence can be seen in a horizontal cross-sectional microscopy image of superficial squamous epithelium. In FIG. 13C, a serial section of the epithelium stained with the anti-EPO primary and Alexa Fluor 594-labeled secondary antibodies reveals numerous eosinophils (red). The DAPI (blue) stain identifies cell nuclei. In FIG. 13D, registration of the microscopy and immunohistochemistry images is reflected by an overlay, supporting the assertion that the microscopy signal originates from eosinophils within the surface epithelium of the esophagus (scale bar, 25 µm).

Thus, the present techniques have been demonstrated to use multi-photon microscopy imaging to identify and quantify eosinophils from esophageal mucosa. The multi-photon microscopy scanning techniques are sensitive to eosinophil autofluorescence from the mucosal surface to a depth of at least about 200 µm. The target-to-background ratio was sufficiently high to distinguish eosinophils from the surrounding squamous epithelium over this depth. The average number of eosinophils on multi-photon microscopy images was found to follow a decaying exponential distribution with a 1/e depth of 62.5 µm, suggesting that most of the infiltrating eosinophils are located within the squamous epithelium. In addition, eosinophils on the microscopy images were found in all of the specimens confirmed as positive on pathology as well as in 5 additional specimens that the pathologist considered negative. Individual microscopy sections provide a representative view of the number of cells seen on conventional histopathology, and were found to have considerable variability over the same dimensions that could lead to diagnostic error or data misinterpretation. Quantifying the number of eosinophils over an epithelial volume of rather than in a single section may achieve greater accuracy and measurement repeatability for EoE diagnosis.

Currently, the diagnosis of EoE relies on a quantitative assessment of eosinophil cell count performed by a pathologist over a region of interest that is determined subjectively on tissue sections that are cut in an arbitrary orientation relative to the mucosal surface. In addition, the results reported are typically the maximum number seen rather than the absolute.

Furthermore, clinical symptoms used to formulate this diagnosis can be nonspecific and difficult to distinguish from GERD. Diagnostic accuracy and disease management can be greatly enhanced by establishing a standardized method for accurately measuring the number of eosinophils over a known tissue volume. The source of this intense multi-photon microscopy signal is believed to be FAD contained within eosinophil granules in high concentrations, distinguishing these cells from other mediators of inflammation, such as neutrophils, lymphocytes, and monocytes. Once diagnosed and treated, patient follow-up can be performed in an objective and consistent manner. This technique can be particularly useful when symptoms persist by providing better quantification of eosinophils to determine optimal therapeutic response and to determine whether future treatments will effectively reduce eosinophil count.

In any event, as shown, multi-photon microscopy imaging represents an effective approach for evaluating EoE by performing an "optical biopsy" of the specimen in a nondestructive, label-free manner. For example, we found that 700 nm was an effective wavelength for 2-photon excitation of the mucosal eosinophils based on our previous study. This result is consistent with the blue shift that has been observed in other studies as well. To address the focal and patchy nature of this disease, miniature 2-photon imaging instruments that are endoscope compatible may be used to collect multi-photon microscopy images in vivo. Multi-photon microscopy imaging can significantly improve tissue penetration depth and achieve 3D imaging with negligible risk of mutagenicity, with improved accuracy for disease detection and therapeutic monitoring.

As shown, the present techniques provide for the design and fabrication of a piezoelectric actuator for miniature multi-photon microscopy and other applications, where the actuator includes multiple stages: a PZT stage; a mechanical amplification stage; and suspended lens-platform stage. The mechanical amplification stage has been optimized by an analytical model and linear and non-linear simulations to provide for sufficient large deflections, while maintaining desired scanning frequency. The actuator may be fabricated using a silicon-on-insulator (SOI) process, for example. With an amplification factor of 170×, the amplifier is able to transform a PZT input displacement of 1.43 μm (at 100 V) into a lens-platform displacement of 486 μm. This nominal design meets the specifications needed for the integration into a two-photon endoscope probe to allow 3D imaging.

While example designs are illustrated above, the present techniques are not limited to the illustrated examples. It will be appreciated that the techniques may be implemented using dual-clad optical fibers for improved emission and collection efficiency. Further, the planar xy-scanning mirror mechanisms may be implemented through any number of suitable scanning modalities, including fiber scanning for very small diameter instruments, scanning with resonant mirrors, and electromagnetic servo-motor scanning. Out-of-plane scanning may be achieved using thermal microactuators, piezoelectric stack actuators, linear DC motor, or hydraulic/pneumatic drives, as examples. Discussed below are example excitation and collection wavelengths; however, the present techniques are not limited to these discussed and indeed may be implemented across different suitable pump beam and florescence wavelengths, in accordance with the sample under examiner.

The multistage, amplifying, fast scanning actuator techniques described herein may be used any number of implementations across any number of applications. The microactuator examples discussed with respect to FIG. 1 are merely provided by way of example, not limitation. This includes the two-photon endoscopic devices discussed in Exhibit B and directed to analyzing eosinophilic esophagitis and nasal rhinitis. In other applications, the techniques herein may be used for cancer detection using peptide or other molecular markers, that are examined at a below tissue surface using a two-photon fluorescence excitation and monitoring resulting from the multistage amplifying actuator. Other biological applications including small animal model testing, which may be explored given the size of the endoscopic devices thanks to large displacement, PZT, multistage MEMS actuator. Examples include directional movement of cancer cells toward blood vessels and cell proliferation of breast cancer cells in mouse models. Other examples include whole or partial organ imaging, particularly in animal models, e.g., brain slice imaging across different depths achievable with the large z-axis control of focusing depth.

Yet, other example applications include imaging drug distribution and nanoparticle transport in biological structures, imaging interaction between cells and surrounding extracellular material, and 3D optical sectioning of living cells.

Furthermore, while examples are described for imaging a biological sample, tissue, it will be appreciated that the present techniques may be used to image a non-biological material, scanning a 2D or 3D volume of a plastic, semiconductor material, or some combination thereof, using different illumination wavelengths capable of sub-surface imaging.

More broadly the techniques herein may be used for any scanning or positioning of a laser energy below the surface of a sample material, biologic or non-biologic (e.g., plastic, semiconductor, metal, etc.) by virtue having an electrically controllable 3D scanning stage.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. An endoscopic device for illuminating a sample over a 3-dimensional volume, the device comprising:
   a connector stage for receiving an input beam of short pulses;
   an xy-scanning stage coupled to receive the input beam of short pulses and scan the short pulses for movement in a lateral direction across an xy-plane of the sample;
   an actuator stage coupled to scan the short pulses for movement in a z-axis direction of the sample, where the actuator stage comprises a piezoelectric stage capable of producing a first displacement, an amplification stage mechanically coupled to the piezoelectric stage for amplifying the first displacement into a second displacement, and a lens mounting stage coupled to the amplification stage, where the piezoelectric stage, the amplification stage, and the lens mounting stage form an integrated MEMS assembly; and
   a lens mounted on the lens mounting stage for scanning the input beam across the 3-dimensional volume within the sample.

2. The endoscopic device of claim 1, wherein the amplification stage comprises a lever amplifier for translating piezoelectric movement into at least partially transverse movement and mechanically coupled to a chevron stage for translating and amplifying the translated movement into longitudinal movement.

3. The endoscopic device of claim 2, wherein the chevron stage comprises two chevron beams coupled to tips of lever beams of the lever amplifier.

4. The endoscopic device of claim 2, wherein the piezoelectric stage is formed of a lead-zirconate-titanate (PZT) assembly rigidly coupled to one end of a base and movably coupled to the amplification stage, wherein the amplification stage is positioned for movement along the base.

5. The endoscopic device of claim 2, wherein the lens mounting stage comprises a lens platform and a spring system coupling the lens platform to the chevron stage.

6. The endoscopic device of claim 1, further comprising a gradient index (GRIN) lens at sampling end of the endoscopic device for coupling the light into the sample.

7. The endoscopic device of claim 1, further comprising an external controller coupled to the xy-scanning stage and to the actuator stage to control scanning of the short pulses within the 3-dimensional volume of the sample.

8. The endoscopic device of claim 1, wherein the sample is a biological sample.

9. The endoscopic device of claim 8, wherein the biological sample is tissue.

10. The endoscopic device of claim 1, wherein the sample is a non-biological material.

11. The endoscopic device of claim 10, wherein the non-biological material comprises a plastic, metal, or semiconductor material.

12. The endoscopic device of claim 1, wherein the actuator stage comprises two opposing actuators housed, along with the xy scanning stage and the lens, within a housing.

13. The endoscopic device of claim 12, wherein the actuator stage scans the short pulses over a range of 0 to 500 μm in the z-axis.

14. The endoscopic device of claim 13, wherein the actuator stage has a scanning frequency of 0 to 500 Hz.

15. The endoscopic device of claim 13, wherein the actuator stage has a scanning frequency of greater than 500 Hz.

* * * * *